US010973801B2

(12) United States Patent
Vandyck et al.

(10) Patent No.: US 10,973,801 B2
(45) Date of Patent: Apr. 13, 2021

(54) CAPSID ASSEMBLY MODULATOR DOSING REGIMEN

(71) Applicant: Janssen Sciences Ireland Unlimited Company, County Cork (IE)

(72) Inventors: Koen Vandyck, Paal-Beringen (BE); Oliver Lenz, Sint-Katelijne Waver (BE); Claire Elisabeth Balmain, Antwerp (BE); Jan Snoeys, Westmalle (BE); Joris Jozef Vandenbossche, Tervuren (BE); Dominique Josiane W. Verstraete, Lokeren (BE); Jeysen Zivan Yogaratnam, Danville, CA (US); Maria Jansens, Turnhout (BE); Frederic Van Dycke, Nijlen (BE)

(73) Assignee: Janssen Sciences Ireland Unlimited Company, Barnahely Ringaskidd (IE)

( * ) Notice: Subject to any disclaimer, the term of this patent is extended or adjusted under 35 U.S.C. 154(b) by 0 days.

(21) Appl. No.: 16/352,754

(22) Filed: Mar. 13, 2019

(65) Prior Publication Data
US 2019/0282542 A1  Sep. 19, 2019

Related U.S. Application Data

(60) Provisional application No. 62/642,997, filed on Mar. 14, 2018.

(51) Int. Cl.
*A61K 31/40* (2006.01)
*A61K 47/38* (2006.01)
*A61K 31/4439* (2006.01)
*A61K 38/21* (2006.01)
*A61K 31/675* (2006.01)
*A61K 31/522* (2006.01)
*A61P 31/20* (2006.01)
*A61K 31/454* (2006.01)

(52) U.S. Cl.
CPC .......... *A61K 31/40* (2013.01); *A61K 31/4439* (2013.01); *A61K 31/454* (2013.01); *A61K 31/522* (2013.01); *A61K 31/675* (2013.01); *A61K 38/21* (2013.01); *A61K 47/38* (2013.01); *A61P 31/20* (2018.01)

(58) Field of Classification Search
CPC ... A61P 31/20; A61K 31/4439; A61K 31/454; A61K 31/522; A61K 31/675; A61K 38/21; A61K 47/38
USPC ..................................................... 546/276.4
See application file for complete search history.

(56) References Cited

U.S. PATENT DOCUMENTS

| | | |
|---|---|---|
| 3,843,662 A | 10/1974 | Holland |
| 4,569,940 A | 2/1986 | Watts |
| 4,962,101 A | 10/1990 | Dininno et al. |
| 4,995,898 A | 2/1991 | Nasu et al. |
| 5,272,167 A | 12/1993 | Girijavallabhan et al. |
| 5,308,826 A | 5/1994 | Chin et al. |
| 5,314,880 A | 5/1994 | Whittaker et al. |
| 5,571,821 A | 11/1996 | Chan et al. |
| 5,585,327 A | 12/1996 | Chin et al. |
| 5,607,929 A | 3/1997 | Nicol |
| 5,708,034 A | 1/1998 | Kleemann et al. |
| 5,723,411 A | 3/1998 | Stevenson |
| 5,756,524 A | 5/1998 | Riordan et al. |
| 5,795,907 A | 8/1998 | Kalindjian et al. |
| 5,912,260 A | 6/1999 | Kalindjian et al. |
| 5,919,970 A | 7/1999 | Song et al. |
| 5,939,423 A | 8/1999 | Karlin |
| 6,025,367 A | 2/2000 | Forbes et al. |
| 6,265,408 B1 | 7/2001 | Forbes et al. |
| 6,476,025 B1 | 11/2002 | Flockerzi et al. |
| 6,562,978 B1 | 5/2003 | Imamura et al. |
| 6,650,463 B2 | 11/2003 | Obikawa et al. |
| 6,668,527 B2 | 12/2003 | Chupak et al. |
| 6,780,389 B2 | 8/2004 | Karl et al. |
| 7,115,595 B2 | 10/2006 | Sunagawa et al. |
| 7,186,735 B2 | 3/2007 | Strobel et al. |
| 7,338,956 B2 | 3/2008 | Strobel et al. |
| 7,368,457 B2 | 5/2008 | Josien et al. |
| 7,384,967 B2 | 6/2008 | Polisetti et al. |
| 7,541,373 B2 | 6/2009 | Polisetti et al. |
| 7,544,700 B2 | 6/2009 | Halazy et al. |
| 7,576,688 B2 | 8/2009 | Lehtinen |
| 7,595,322 B2 | 9/2009 | Morgan et al. |
| 7,608,723 B2 | 10/2009 | Boyce et al. |
| 7,750,158 B2 | 7/2010 | Shankar et al. |
| 7,786,104 B2 | 8/2010 | Dubois et al. |
| 7,790,726 B2 | 9/2010 | Zhang et al. |
| 7,838,525 B2 | 11/2010 | Jones et al. |
| 7,888,373 B2 | 2/2011 | Morgan et al. |
| 7,994,168 B2 | 8/2011 | Lennig et al. |

(Continued)

FOREIGN PATENT DOCUMENTS

CA   2950807 A1   12/2015
CN   101039919 A   9/2007

(Continued)

OTHER PUBLICATIONS

Aljaberi; Drug Development and Industrial Pharmacy, 2009, 35, 1066-1071. (Year: 2009).*
Edge; International Journal of Pharmaceutics 2000, 200, 67-72. (Year: 2000).*
Nokhodchi; BioImpacts 2012, 2, 175-187. (Year: 2012).*
Tobyn; International Journal of Pharmaceutics 1998, 169, 183-194. (Year: 1998).*

(Continued)

*Primary Examiner* — Daniel R Carcanague

(74) *Attorney, Agent, or Firm* — Lathrop GPM LLP; Brian C. Trinque

(57) ABSTRACT

The present disclosure is directed to methods of using a capsid assembly inhibitor for the treatment of hepatitis B virus infection.

18 Claims, 5 Drawing Sheets

(56) References Cited

U.S. PATENT DOCUMENTS

| | | |
|---|---|---|
| 8,071,779 B2 | 12/2011 | Richards et al. |
| 8,084,457 B2 | 12/2011 | Choidas et al. |
| 8,097,728 B2 | 1/2012 | Gu et al. |
| 8,101,620 B2 | 1/2012 | Morgan et al. |
| 8,153,650 B2 | 4/2012 | Dubois et al. |
| 8,153,803 B2 | 4/2012 | Kazantsev et al. |
| 8,207,195 B2 | 6/2012 | Navratil et al. |
| 8,227,489 B2 | 7/2012 | Dubois et al. |
| 8,273,754 B2 | 9/2012 | Hill et al. |
| 8,299,096 B2 | 10/2012 | Navratil et al. |
| 8,299,114 B2 | 10/2012 | Dubois et al. |
| 8,354,425 B2 | 1/2013 | Dubois et al. |
| 8,394,820 B2 | 3/2013 | Dubois et al. |
| 8,399,491 B2 | 3/2013 | Dubois et al. |
| 8,404,747 B2 | 3/2013 | Kazantsev et al. |
| 8,410,141 B2 | 4/2013 | Murata et al. |
| 8,410,147 B2 | 4/2013 | Peterson et al. |
| 8,536,168 B2 | 9/2013 | Dai et al. |
| 8,597,949 B2 | 12/2013 | Connell et al. |
| 8,609,668 B2 | 12/2013 | Cuconati et al. |
| 8,629,274 B2 | 1/2014 | Hartman et al. |
| 8,697,685 B2 | 4/2014 | Axten et al. |
| 8,722,742 B2 | 5/2014 | Reyes et al. |
| 8,808,702 B2 | 8/2014 | Reddy et al. |
| 8,889,716 B2 | 11/2014 | Prime et al. |
| 8,993,771 B2 | 3/2015 | Hartman et al. |
| 9,040,033 B2 | 5/2015 | Miller et al. |
| 9,051,296 B2 | 6/2015 | Yamagishi et al. |
| 9,061,008 B2 | 6/2015 | Hartman et al. |
| 9,066,932 B2 | 6/2015 | Hartman et al. |
| 9,115,101 B2 | 8/2015 | Bodil Van Niel et al. |
| RE45,670 E | 9/2015 | Polisetti et al. |
| 9,156,839 B2 | 10/2015 | Vandyck et al. |
| 9,169,212 B2 | 10/2015 | Hartman et al. |
| 9,181,288 B2 | 11/2015 | Hartman et al. |
| 9,205,079 B2 | 12/2015 | Hartman et al. |
| 9,339,510 B2 | 5/2016 | Hartman et al. |
| 9,400,280 B2 | 7/2016 | Hartman |
| 9,422,323 B2 | 8/2016 | Houpis et al. |
| 9,458,176 B2 | 10/2016 | Takaishi et al. |
| 9,505,722 B2 | 11/2016 | Hartman et al. |
| 9,567,299 B2 | 2/2017 | Vandyck et al. |
| 9,579,313 B2 | 2/2017 | Hartman |
| 9,676,747 B2 | 6/2017 | Hartman et al. |
| 9,884,818 B2 | 2/2018 | Vandyck et al. |
| 10,071,961 B2 | 9/2018 | Vandyck et al. |
| 10,125,094 B2 | 11/2018 | Vandyck et al. |
| 10,441,589 B2 * | 10/2019 | Hartman ............... A61K 31/40 |
| 10,457,638 B2 * | 10/2019 | Vandyck ............... A61K 45/06 |
| 2002/0049236 A1 | 4/2002 | Chupak et al. |
| 2003/0022944 A1 | 1/2003 | Gumkowski et al. |
| 2003/0114443 A1 | 6/2003 | Imamura et al. |
| 2003/0163931 A1 | 9/2003 | Beyerinck et al. |
| 2003/0224043 A1 | 12/2003 | Appel et al. |
| 2004/0039009 A1 | 2/2004 | Jagtap et al. |
| 2004/0110802 A1 | 6/2004 | Thorarensen et al. |
| 2004/0254183 A1 | 12/2004 | Basarab et al. |
| 2005/0009871 A1 | 1/2005 | Ramesh et al. |
| 2005/0054850 A1 | 3/2005 | Wu et al. |
| 2005/0129833 A1 | 6/2005 | Kincaid et al. |
| 2005/0148632 A1 | 7/2005 | Tokumasu et al. |
| 2005/0221272 A1 | 10/2005 | Housman et al. |
| 2005/0239833 A1 | 10/2005 | Kazantsev et al. |
| 2006/0040984 A1 | 2/2006 | Luckhurst et al. |
| 2006/0079543 A1 | 4/2006 | Sum et al. |
| 2006/0100228 A1 | 5/2006 | Shankar et al. |
| 2006/0100257 A1 | 5/2006 | Muto et al. |
| 2006/0122236 A1 | 6/2006 | Wood et al. |
| 2007/0142440 A1 | 6/2007 | Burgdorf et al. |
| 2007/0161578 A1 | 7/2007 | Hwa et al. |
| 2007/0265262 A1 | 11/2007 | Schmitz et al. |
| 2008/0234270 A1 | 9/2008 | Canne et al. |
| 2008/0262107 A1 | 10/2008 | Babcock et al. |
| 2009/0018118 A1 | 1/2009 | Urleb et al. |
| 2009/0036420 A1 | 2/2009 | Galley et al. |
| 2009/0105218 A1 | 4/2009 | Ulven et al. |
| 2009/0163545 A1 | 6/2009 | Goldfarb |
| 2009/0259044 A1 | 10/2009 | Kazantsev |
| 2009/0325959 A1 | 12/2009 | Vittitow et al. |
| 2009/0325960 A1 | 12/2009 | Fulcher et al. |
| 2010/0008968 A1 | 1/2010 | Lampe et al. |
| 2010/0016310 A1 | 1/2010 | Ingraham |
| 2010/0022517 A1 | 1/2010 | Richards et al. |
| 2010/0029667 A1 | 2/2010 | Ketner et al. |
| 2010/0087415 A1 | 4/2010 | Whitten et al. |
| 2010/0113421 A1 | 5/2010 | Williams et al. |
| 2010/0166864 A1 | 7/2010 | Gadre et al. |
| 2010/0204210 A1 | 8/2010 | Sorensen et al. |
| 2010/0292232 A1 | 11/2010 | Elleder et al. |
| 2011/0009622 A1 | 1/2011 | Jitsuoka et al. |
| 2011/0064695 A1 | 3/2011 | Qiu et al. |
| 2011/0064696 A1 | 3/2011 | Or et al. |
| 2011/0065686 A1 | 3/2011 | Mazola et al. |
| 2011/0184019 A1 | 6/2011 | Zitzmann et al. |
| 2011/0189771 A1 | 8/2011 | Block et al. |
| 2011/0275630 A1 | 11/2011 | Matulenko et al. |
| 2011/0294902 A1 | 12/2011 | Curatolo et al. |
| 2011/0301158 A1 | 12/2011 | Polisetti et al. |
| 2012/0202763 A1 | 8/2012 | Almstead et al. |
| 2013/0005756 A1 | 1/2013 | Vittitow et al. |
| 2013/0131059 A1 | 5/2013 | Lampe et al. |
| 2013/0131106 A1 | 5/2013 | Lampe et al. |
| 2013/0142827 A1 | 6/2013 | Block et al. |
| 2013/0203733 A1 | 9/2013 | Kazantsev et al. |
| 2013/0251673 A1 | 9/2013 | Hartman et al. |
| 2013/0267517 A1 | 10/2013 | Guo et al. |
| 2013/0303552 A1 | 11/2013 | Xu et al. |
| 2014/0178337 A1 | 6/2014 | Hartman et al. |
| 2014/0179665 A1 | 6/2014 | Hartman et al. |
| 2014/0275167 A1 | 9/2014 | Hartman |
| 2015/0152073 A1 | 6/2015 | Hartman et al. |
| 2015/0174115 A1 | 6/2015 | Hartman et al. |
| 2015/0175602 A1 | 6/2015 | Brown et al. |
| 2015/0197493 A1 | 7/2015 | Hartman |
| 2015/0197533 A1 | 7/2015 | Hartman et al. |
| 2015/0216938 A1 | 8/2015 | Hartman |
| 2015/0225355 A1 | 8/2015 | Hartman |
| 2015/0252057 A1 | 9/2015 | Guo et al. |
| 2015/0259324 A1 | 9/2015 | Hartman et al. |
| 2015/0266890 A1 | 9/2015 | Vandyck et al. |
| 2015/0274652 A1 | 10/2015 | Hartman |
| 2015/0274653 A1 | 10/2015 | Vandyck et al. |
| 2016/0000812 A1 | 1/2016 | Hartman et al. |
| 2016/0002155 A1 | 1/2016 | Vandyck et al. |
| 2016/0051512 A1 | 2/2016 | Vandyck et al. |
| 2016/0083383 A1 | 3/2016 | Guo et al. |
| 2016/0115125 A1 * | 4/2016 | Vandyck ............... C07D 403/12 514/422 |
| 2016/0115149 A1 | 4/2016 | Vandyck et al. |
| 2016/0158214 A1 | 6/2016 | Hartman |
| 2016/0176817 A1 | 6/2016 | Vandyck et al. |
| 2016/0272599 A1 | 9/2016 | Hartman et al. |
| 2016/0347741 A1 * | 12/2016 | Vandyck ............... A61K 31/4545 |
| 2017/0002025 A1 | 1/2017 | Vendeville et al. |
| 2017/0015629 A1 | 1/2017 | Hartman |
| 2017/0114018 A1 | 4/2017 | Hartman |
| 2017/0158634 A1 | 6/2017 | Vandyck et al. |
| 2017/0182021 A1 | 6/2017 | Hartman |
| 2017/0334882 A1 | 11/2017 | Hartman et al. |
| 2017/0340642 A1 * | 11/2017 | Hartman ............... A61K 31/445 |
| 2018/0141905 A1 | 5/2018 | Vandyck et al. |
| 2019/0365767 A1 * | 12/2019 | Hartman ............... A61K 31/7072 |
| 2020/0039931 A1 * | 2/2020 | Vandyck ............... C07D 207/40 |
| 2020/0330499 A1 * | 10/2020 | Biermer ............... A61K 31/713 |
| 2020/0332297 A1 * | 10/2020 | Biermer ............... A61K 31/40 |

FOREIGN PATENT DOCUMENTS

| | | |
|---|---|---|
| CN | 102093320 A | 6/2011 |
| CN | 102206172 A | 10/2011 |
| EP | 0 232 067 A2 | 8/1987 |
| EP | 0 742 200 B1 | 7/1999 |
| EP | 1269994 A2 | 1/2003 |
| EP | 1027885 A3 | 1/2007 |

(56) References Cited

FOREIGN PATENT DOCUMENTS

| | | |
|---|---|---|
| EP | 1745774 A3 | 4/2007 |
| EP | 2 280 001 A1 | 2/2011 |
| EP | 3653630 A1 | 5/2020 |
| JP | S62-142164 A | 6/1987 |
| JP | 2008-525406 A | 7/2008 |
| JP | 2008-179621 A | 8/2008 |
| JP | 2010-535172 A | 11/2010 |
| WO | 1984/003281 A1 | 8/1984 |
| WO | 1992/007835 A1 | 5/1992 |
| WO | 1998/023285 A1 | 6/1998 |
| WO | 1999/009022 A1 | 2/1999 |
| WO | 1999/038845 A1 | 8/1999 |
| WO | 1999/048492 A1 | 9/1999 |
| WO | 1999/065906 A1 | 12/1999 |
| WO | 2001/005390 A2 | 1/2001 |
| WO | 2001/019788 A2 | 3/2001 |
| WO | WO 2001/025200 A1 | 4/2001 |
| WO | 2001/047495 A1 | 7/2001 |
| WO | 2001/051487 A1 | 7/2001 |
| WO | 2001/055121 A1 | 8/2001 |
| WO | 2001/085694 A2 | 11/2001 |
| WO | 2002/051410 A2 | 7/2002 |
| WO | 2002/064618 A2 | 8/2002 |
| WO | 2003/000295 A3 | 1/2003 |
| WO | 2003/007955 A2 | 1/2003 |
| WO | WO 2003/002518 A1 | 1/2003 |
| WO | 2003/044016 A1 | 5/2003 |
| WO | 2003/063821 A2 | 8/2003 |
| WO | 2003/063822 A2 | 8/2003 |
| WO | 2003/063831 A3 | 8/2003 |
| WO | 2003/101961 A1 | 12/2003 |
| WO | 2004/010943 A2 | 2/2004 |
| WO | 2004/011427 A2 | 2/2004 |
| WO | 2004/022060 A2 | 3/2004 |
| WO | 2004/058709 A1 | 7/2004 |
| WO | 2004/086865 A1 | 11/2004 |
| WO | 2004/099192 A2 | 11/2004 |
| WO | 2004/100947 A2 | 11/2004 |
| WO | 2005/016922 A2 | 2/2005 |
| WO | 2005/044797 A1 | 5/2005 |
| WO | WO 2005/000231 A3 | 5/2005 |
| WO | 2005/087217 A1 | 9/2005 |
| WO | 2005/105785 A2 | 11/2005 |
| WO | 2005/115330 A2 | 12/2005 |
| WO | 2005/115374 A1 | 12/2005 |
| WO | 2006/002133 A1 | 1/2006 |
| WO | WO 2006/012642 A2 | 2/2006 |
| WO | 2006/024834 A1 | 3/2006 |
| WO | 2006/053109 A1 | 5/2006 |
| WO | 2006/067445 A2 | 6/2006 |
| WO | 2006/067446 A1 | 6/2006 |
| WO | 2006/107593 A2 | 10/2006 |
| WO | 2006/123257 A2 | 11/2006 |
| WO | 2006/128129 A2 | 11/2006 |
| WO | 2006/128172 A2 | 11/2006 |
| WO | 2007/031791 A1 | 3/2007 |
| WO | 2007/070556 A2 | 6/2007 |
| WO | 2008/011476 A2 | 1/2008 |
| WO | 2008/022171 A1 | 2/2008 |
| WO | 2008/047201 A2 | 4/2008 |
| WO | WO 2008/054605 A2 | 5/2008 |
| WO | 2008/093614 A1 | 8/2008 |
| WO | 2008/137794 A1 | 11/2008 |
| WO | 2008/154819 A1 | 12/2008 |
| WO | 2009/016088 A1 | 2/2009 |
| WO | WO 2009/018219 A2 | 2/2009 |
| WO | 2009/062402 A1 | 5/2009 |
| WO | 2009/086303 A2 | 7/2009 |
| WO | 2009/131065 A1 | 10/2009 |
| WO | 2009/146013 A1 | 12/2009 |
| WO | 2010/018113 A2 | 2/2010 |
| WO | 2010/043592 A1 | 4/2010 |
| WO | WO 2010/059658 A1 | 5/2010 |
| WO | 2010/088000 A2 | 8/2010 |
| WO | 2010/123139 A1 | 10/2010 |
| WO | WO 2010/123139 A1 | 10/2010 |
| WO | WO 2010/138758 A1 | 12/2010 |
| WO | 2011/002635 A1 | 1/2011 |
| WO | 2011/035143 A2 | 3/2011 |
| WO | 2011/088015 A1 | 7/2011 |
| WO | 2011/088561 A1 | 7/2011 |
| WO | 2011/109237 A2 | 9/2011 |
| WO | 2011/112191 A1 | 9/2011 |
| WO | 2011/123609 A1 | 10/2011 |
| WO | 2011/140324 A1 | 11/2011 |
| WO | 2011/155898 A1 | 12/2011 |
| WO | 2011/159626 A1 | 12/2011 |
| WO | 2012/016133 A2 | 2/2012 |
| WO | 2012/018635 A2 | 2/2012 |
| WO | 2012/033956 A1 | 3/2012 |
| WO | 2012/049277 A1 | 4/2012 |
| WO | 2012/075235 A1 | 6/2012 |
| WO | 2012/080050 A1 | 6/2012 |
| WO | 2012/117216 A1 | 9/2012 |
| WO | 2012/136834 A1 | 10/2012 |
| WO | 2013/006394 A1 | 1/2013 |
| WO | 2013/096744 A1 | 6/2013 |
| WO | 2013/102655 A1 | 7/2013 |
| WO | 2013/130703 A2 | 9/2013 |
| WO | WO 2013/144129 A1 | 10/2013 |
| WO | WO 2013/174962 A1 | 11/2013 |
| WO | 2013/181584 A2 | 12/2013 |
| WO | 2013/184757 A1 | 12/2013 |
| WO | 2014/033167 A1 | 3/2014 |
| WO | 2014/033170 A1 | 3/2014 |
| WO | 2014/033176 A1 | 3/2014 |
| WO | 2014/037480 A1 | 3/2014 |
| WO | 2014/106019 A2 | 7/2014 |
| WO | 2014/126969 A1 | 8/2014 |
| WO | 2014/131847 A1 | 9/2014 |
| WO | 2014/137777 A1 | 9/2014 |
| WO | 2014/151958 A1 | 9/2014 |
| WO | 2014/161888 A1 | 10/2014 |
| WO | WO 2014/165128 A2 | 10/2014 |
| WO | 2014/184350 A1 | 11/2014 |
| WO | 2014/184365 A1 | 11/2014 |
| WO | WO 2014/184328 A1 | 11/2014 |
| WO | 2014/191301 A1 | 12/2014 |
| WO | 2014/191726 A1 | 12/2014 |
| WO | 2014/198880 A1 | 12/2014 |
| WO | 2015/011281 A1 | 1/2015 |
| WO | 2015/055764 A1 | 4/2015 |
| WO | 2015/057945 A1 | 4/2015 |
| WO | 2015/059212 A1 | 4/2015 |
| WO | 2015/073774 A1 | 5/2015 |
| WO | 2015/109130 A1 | 7/2015 |
| WO | 2015/116923 A1 | 8/2015 |
| WO | 2015/118057 A1 | 8/2015 |
| WO | 2015/138895 A1 | 9/2015 |
| WO | WO 2015/132276 A1 | 9/2015 |
| WO | 2015/144093 A1 | 10/2015 |
| WO | 2015/180631 A1 | 12/2015 |
| WO | 2016/089990 A1 | 6/2016 |
| WO | 2016/109663 A2 | 7/2016 |
| WO | 2016/109684 A2 | 7/2016 |
| WO | 2016/109689 A2 | 7/2016 |
| WO | 2016/113273 A1 | 7/2016 |
| WO | 2016/149581 A1 | 9/2016 |
| WO | 2016/161268 A1 | 10/2016 |
| WO | 2016/168619 A1 | 10/2016 |
| WO | 2016/183266 A1 | 11/2016 |
| WO | 2017181141 A1 | 10/2017 |
| WO | WO 2019/011323 A1 | 1/2019 |
| WO | WO2020183020 A1 * | 9/2020 ............ A61K 31/40 |
| WO | WO 2020255012 * | 12/2020 ............ A61K 31/18 |

OTHER PUBLICATIONS

Written Opinion in International Application PCT/EP2020/056991, dated Sep. 17, 2020, 6 pages. (Year: 2020).*
The Merck Index (2013) "Zidovudine," An Encyclopedia of Chemicals, Drugs and Biologicals. 15th Ed. p. 10324.

(56) References Cited

OTHER PUBLICATIONS

Thompson et al. (2007) "Toll-like receptors, RIG-I-like RNA helicases and the antiviral innate immune response," Immunology and Cell Biology. 85:435-445.
Weber et al. (2002) "Inhibition of human hepatitis B virus (HBV) by a novel non-nucleosidic compound in a transgenic mouse model," Antiviral Res. 54:69-78.
West (1984) Solid State Chemistry and its Applications. John Wiley & Sons. pp. 33-36.
Yarmolchuk (2011) "Synthesis of β-fluoro-β-proline," Tetrahedron Letters. 51(12):1300-1302.
Zhang et al. (2005) "A Potent Small Molecule Inhibits Polyglutamine Aggregation in Huntington's Disease Neurons and Suppresses Neurodegeneration in vivo," Proc. Natl. Acad. Sci. USA. 102(3):892-897.
[online] Registry via SciFinfer, Feb. 13, 2017, RN 1208400-27-4.
Brahmania (Jan. 13, 2016) "New therapeutic agents for chronic hepatitis B," Lancet Infect. Dis. 16(2):e10-e21.
Brezillon et al. (2011) "Antiviral activity of Bay 41-4109 on hepatitis B virus in humanized Alb-uPA/SCID mice," PLoS One. 6:e25096. pp. 1-6.
Chang et al. (2007) "NMR-spectroscopy-based metabonomic approach to the analysis of Bay41-4109, a novel anti-HBV compound, induced hepatotoxicity in rats," Tox. Letters. 173:161-167.
Cho et al. (Dec. 25, 2013) "2-amino-N-(2,6-dichloropyridin-3-yl)acetamide derivatives as a novel class of HBV capsid assembly inhibitor," Viral Hep. 21:843-852.
Cowie et al. (Jun. 11, 2013) "Mortality due to viral hepatitis in the Global Burden of Disease Study 2010: new evidence of an urgent global public health priority demanding action," Antivir. Ther. 18:953-954.
Delaney et al. (2002) "Phenylpropenamide derivatives AT-61 and AT-130 inhibit replication of wild-type and lamivudine-resistant strains of hepatitis B virus in vitro," Antimicrob. Agents Chemother. 46:3057-3060.
Deres et al. (2003) "Inhibition of hepatitis B virus replication by drug-induced depletion of nucleocapsids," Science. 299:893-896.
Gane (2014) "Phase 1a Saftey and Pharmacokinetics of NVR 3-778, a Potential First-in-Class HBV Core Inhibitor," In; The Abstracts of the Liver Meeting 2014 (AASLD). Boston, MA. Abstract LB-19.
Guo (2011) "HBc binds to the CpG islands of HBV cccDNA and promotes an epigenetic permissive state," Epigenetics. 6:720-726.
Huang et al. (Oct. 2016) "Blockage of HBV Virus Replication and Inhibition of cccDNA Establishment by Core Protein Allosteric Modifiers (CpAMs)," In; The Abstracts of the Liver Meeting 2016 (AASLD). Boston, MA. po. 937A-938A. Abstract 1897.
Katen et al. (Jul. 18, 2013) "Assembly-directed antivirals differentially bind quasiequivalent pockets to modify hepatitis B virus capsid tertiary and quaternary structure," Structure. 21(8):1406-1416.
Klumpp et al. (2015) "O115: High antiviral activity of the HBV core inhibitor NVR 3-778 in the humanized uPA/SCID mouse model," J. Hepatol. 62:S250.
Klumpp et al. (Nov. 23, 2015) "High-resolution crystal structure of a hepatitis B virus replication inhibitor bound to the viral core protein," Proc. Natl. Acad. Sci. 112:15196-15201.
Lam et al. (Oct. 2015) "Inhibition of Hepatitis B Virus Replication by the HBV Core Inhibitor NVR 3-778," In; The Abstracts of the Liver Meeting 2015 (AASLD). San Francisco, CA. p. 223A. Abstract 33.
Lam et al. (Oct. 2016) "HBV Core Assembly Modulators Block Antigen Production when Present during Infection, but not during Persistent Infection," In; The Abstracts of the Liver Meeting 2016 (AASLD). Boston, MA. p. 913A. Abstract 1850.
Lam et al. (Sep. 2016) "Serum HBV RNA as a Pharmacodynamic (PD) Marker of HBV Treatment Response to Core Assembly Modulator NVR 3-778 and Pegylated-Interferon Alpha," Poster Presented In; The AASLD/EASL HBV Treatment Endpoints Workshop. Alexandria, VA. Sep. 8-9, 2016. Poster No. 3774.

Lucifora et al. (Feb. 20, 2014) "Specific and nonhepatotoxic degradation of nuclear hepatitis B virus cccDNA," Science. 343:1221-1228.
Manzoor et al. (Nov. 28, 2015) "Hepatitis B virus therapy: What's the future holding for us?" World J Gastro. 21:12558-12575.
Qiu et al. (Aug. 10, 2016) "Design and Synthesis of Orally Bioavailable 4-Methyl Heteroaryldihydropyrimidine Based Hepatitis B Virus (HBV) Capsid Inhibitors," J. Med. Chem. 59:7651-7666.
Stray et al. (2005) "A heteroaryldihydropyrimidine activates and can misdirect hepatitis B virus capsid assembly," Proc. Natl. Acad. Sci. USA. 102:8138-8143.
Stray et al. (2006) "Bay 41-4109 has multiple effects on Hepatitis B virus capsid assembly," J. Mol. Recognit. 19:542-548.
Tan et al. (Jan. 2, 2013) "Genetically altering the thermodynamics and kinetics of hepatitis B virus capsid assembly has profound effects on virus replication in cell culture," J. Vir. 87:3208-3216.
Wang et al. (Jun. 6, 2012) "In vitro inhibition of HBV replication by a novel compound, GLS4, and its efficacy against adefovir-dipivoxil-resistant HBV mutations," Antiviral therapy 17:793-803.
Wang et al. (May 28, 2016) "Serum hepatitis B virus RNA is encapsidated pregenome RNA that may be associated with persistence of viral infection and rebound," J. Hepatol. 65:700-710.
Wu et al. (Aug. 19, 2013) "Preclinical characterization of GLS4, an inhibitor of hepatitis B virus core particle assembly," Antimicrob. Agents Chemother. 57:5344-5354.
Yang et al. (2016) "Effect of a hepatitis B virus inhibitor, NZ-4, on capsid formation," Antiviral Res. 125:25-33.
Yang et al. (Feb. 3, 2014) "Isothiafludine, a novel non-nucleoside compound, inhibits hepatitis B virus replication through blocking pregenomic RNA encapsidation," Acta Pharmacol. Sin. 35:410-418.
Yogaratnam et al. (Oct. 2016) "Safety, Tolerability and Pharmacokinetics of JNJ-56136379, a Novel HBV Caspid Assembly Modulator, in Healthy Subjects," In; The Abstracts of the Liver Meeting 2016 (AASLD). Boston, MA. po. 930A-931A. Abstract 1881.
Yuen et al. (Apr. 2016) "NVR 3-778, a first-in-class HBV Core inhibitor, alone and incombination with Peg-interferon (PEGIFN), in treatment naive HBeAg-Positive patients: early reductions in HBV DNA and HBeAg," In; The Abstracts of the International Liver Congress (EASL). pp. S210-S211. Abstract LB-06.
Yuen et al. (Oct. 2015) "Phase 1b Efficacy and Safety of NVR 3-778, a First-In-Class HBV Core Inhibitor, in HBeAg-Positive Patients with Chronic HBV Infection," In; The Abstracts of the Liver Meeting 2015 (AASLD). San Francisco, CA. pp. 1385A-1386A. Abstract LB-10.
Zlotnick et al. (Jun. 27, 2015) "Core protein: A pleiotropic keystone in the HBV lifecycle," Antiviral Research. 121:82-93.
Zoulim et al. (Jun. 15, 2016) "Current treatments for chronic hepatitis B virus infections," Curr. Opin. Virol. 18:109-116.
International Search Report and Written Opinion for International Application No. PCT/EP2015/052389, dated Mar. 31, 2015.
International Search Report and Written Opinion for International Application No. PCT/US2017/027802, dated Dec. 15, 2017.
Horig et al. (2004) "From bench to clinic and back: Perspective on the 1st IQPC Translational Research conference," Journal of Translational Medicine, 2(44):1-8.
Mohebbi et al. (2018) "An overview of hepatitis B Virus surface antigen secretion inhibitors," Frontiers in Microbiology, 9(662):1-9.
Nathans et al. (2008) "Small molecule inhibition of HIV-1 vif," Nature Biotechnology 26(10):1187-1192.
Schafer et al. (2008) "Failure is an option: learning from unsuccessful proof-of-concept trials," Drug Discovery Today, 13(21/22):913-916.
Hepatitis B Factsheet, World Health Organization, 2013; Hoofnagle JH, et al., Management of Hepatitis B: Summary of a Clinical Research Workshop, Hepatology, 2007, 45(4):1056-1075.
EASL Clinical Practice Guidelines: Management of chronic hepatitis B virus infection, J. Hepatology, 2012, 57:167-185 (EASL 2012).
Lesmana LA, et al. "Hepatitis B: overview of the burden of disease in the Asia-Pacific region", Liver International, 2006, 26:3-10.
Lok ASF and McMahon BJ, "Chronic Hepatitis B: Update 2009", Hepatology, Sep. 2009:1-36 (Lok 2009) Forthcoming.

(56) References Cited

OTHER PUBLICATIONS

Remington's Pharmaceutical Sciences, 17th ed., Mack Publishing Company, Easton, Pa., 1985, p. 1418.
Berge et al., "Pharmaceutical Salts", Journal of Pharmaceutical Science, 66, issue 1, pp. 1-19 (1977).
Holford, N. H. G. and Scheiner, L. B., "Understanding the Dose-Effect Relationship: clinical Application of Pharmacokinetic-Pharmacodynamic Models", Clin. Pharmacokinet. 6: 429-453 (1981).
Loewe, S. and Muischnek, H., Arch. Exp. Pathol Pharmacol. 114: 313-326 (1926).
Chou, T. C. And Talalay, P., "Quantitative Analysis of Dose-Effect Relationships: The Combined Effects of Multiple Drugs or Enzyme Inhibitors", Adv. Enzyme Regul. 22: 27-55 (1984).
Chou, T-C "Theoretical Basis, Experimental Design, and Computerized Simulation of Synergism and Antagonism in Drug Combination Studies", Pharmacol. Rev. 58: 621-681 (2006).
[online] CAS (STN), 148:183450, RN 296790-26-6, Oct. 18, 2000.
[online] Registry via STN, Jun. 5, 2011, RN 1291044-81-9.
[online] Registry via STN, Jul. 10, 2008, RN 1057788-44-9.
[online] Registry via STN, Jul. 10, 2008, RN 1057871-39-2.
[online] Registry via STN, Aug. 15, 2011, RN 1317923-24-2.
[online] Registry via STN, Aug. 15, 2011, RN 1318022-74-0.
[online] Registry via STN, May 18, 2011, RN 1296380-95-4.
[online] Registry via STN, Oct. 18, 2000, RN 296894-70-7.
[online] Registry via STN, Sep. 20, 2013, RN 1452780-00-5.
Bennes et al. (2001) "Recognition-induced control and acceleration of a pyrrole Diels-Alder reaction," Tetrahedron Letters. 42(12):2377-2380.
Berke et al. (Oct. 2016) "Caspid assembly modulator JNJ-56136379 prevents de novo infection of primary human hepatocytes with hepatitis B virus," In; The Abstracts of the Liver Meeting 2016 (AASLD). Boston, MA. p. 124A. Abstract 234.
Cai et al. (Aug. 2012) "Identification of Disubstituted Sulfonamide Compounds as specific Inhibitors of Hepatitis B Virus Covalently Closed Circular DNA Formation," Antimicrobial Agents and Chemotherapy. 56(8):4277-4288.
Campagna et al. (Apr. 10, 2013) "Sulfonamoylbenzamides Derivatives Inhibit the Assembly of Hepatitis B virus in Nucleocapsids," J. Virol. 87(12):6931-6942.
Duan et al. (2009) "2-Phenylquinazolin-4(3H)-one, a class of potent PDE5 inhibitors with high selectivity versus PDE6," Bioorganic and Medicinal Chemistry. 19(10):2777-2779.
El-Sayed (1998) "A Comparative Study of the Reactions of Thiophene-2-Carboxanilides and Related Compounds," Chemistry of Heterocyclic Compounds. 34(7):796-801.
El-Sharief et al. (1987) "Synthesis of different types of chlorinated sulfonamides with expected insecticidal and bactericidal activities," Proceedings of the Indian National Science Academy, Part A: Physical Sciences. 53(1):179-188.
Ermann et al. (2008) "Arylsulfonamide CB2 receptor agonists: SAR and optimization of CB2 selectivity," Bioorganic & Medicinal Chemistry Letters. 18(5):1725-1729.
Extended European Search Report corresponding to European Patent Application No. 12182076, dated Apr. 19, 2013.
Extended European Search Report corresponding to European Patent Application No. 13157232, dated Apr. 5, 2013.
Extended European Search Report corresponding to European Patent Application No. 13162131, dated Sep. 11, 2013.
Extended European Search Report corresponding to European Patent Application No. 13168291, dated Jun. 20, 2013.
Extended European Search Report corresponding to European Patent Application No. 13168295, dated Oct. 7, 2013.
Extended European Search Report corresponding to European Patent Application No. 13169574, dated Aug. 19, 2013.
Geies (1991) "Synthesis of Some Thiazolo-[3, 2=A]Pyrimidines," Phosphorous, Sulfur and Silicon and the Related Elements. 56(1-4):87-93.
Hogan (2009) "Aqueous Process Chemistry: The Preparation of Aryl Sulfonyl Chlorides," Organic Process Research and Development. 13(5):875-879.
International Search Report with Written Opinion corresponding to International Patent Application No. PCT/EP2013/067821, dated Nov. 28, 2013.
International Search Report with Written Opinion corresponding to International Patent Application No. PCT/EP2013/067829, dated Jan. 10, 2014.
International Search Report with Written Opinion corresponding to International Patent Application No. PCT/EP2014/053858, dated May 28, 2014.
International Search Report with Written Opinion corresponding to International Patent Application No. PCT/EP2014/056601, dated Jun. 13, 2014.
International Search Report with Written Opinion corresponding to International Patent Application No. PCT/EP2014/060102, dated Jul. 7, 2014.
International Search Report with Written Opinion corresponding to International Patent Application No. PCT/EP2014/060132, dated Jun. 16, 2014.
International Search Report with Written Opinion corresponding to International Patent Application No. PCT/US2012/071195, dated Apr. 26, 2013.
International Search Report with Written Opinion corresponding to International Patent Application No. PCT/US2014/024509, dated Oct. 22, 2014.
International Search Report with Written Opinion corresponding to International Patent Application No. PCT/US2015/011663, dated Apr. 29, 2015.
International Search Report with Written Opinion corresponding to International Patent Application No. PCT/US2015/014663, dated Apr. 29, 2015.
International Search Report with Written Opinion corresponding to International Patent Application No. PCT/US2016/023066, dated May 11, 2016.
International Search Report with Written Opinion corresponding to International Patent Application No. PCT/US2016/054424, dated Nov. 21, 2016.
Kim et al. (Apr. 9, 2011) "Discovery of novel HCV polymerase inhibitors using pharmacophore-based virtual screening," Bioorganic and Medicinal Chemistry. 21(11):3329-3334.
Lambeng et al. (2007) "Arylsulfonamides as a new class of cannabinoid CB1 receptor ligands: Identification of a lead and initial SAR studies," Bioorganic & Medicinal Chemistry Letters. 17(1):272-277.
Lau et al. (2005) "Peginterferon Alfa-2a, Lamivudine, and the Combination for HBeAg-Positive Chronic Hepatitis B," The New England Journal of Medicine. 352(26):2682-2695.
Liaw et al. (2009) "Hepatitis B virus infection," Lancet. 373:582-592.
Mabrouck (2012) "Discovering Best Candidates for Hepatocellular Carcinoma (HCC) by in-Silica Techniques and Tools," International Journal of Bioinformatics Research and Applications. 8(1-2):141-152.
Marcellin et al. (2004) "Peginterferon Alfa-2a Alone, Lamivudine Alone, and the Two in Combination in Patients with HBeAg-Negative Chronic Hepatitis B," New Engl. J. Med. 351(12):1206-1217.
Mohamed et al. (1986) "Synthesis of different types of chlorinated sulfonamides with expected insecticidal and antimicrobial activities," Acta Pharmaceutica Jugoslavica. 36(3):301-310.
Patani et al. (1996) "Bioisosterism: A Rational Approach in Drug Design," Chem. Rev. 96:3147-3176.
Patel et al. (2005) "Synthesis N-ethylpiperazinyl Sulfonyl Group Incorporated Benzamides" Indian Journal of Heterocyclic Chemistry. 15:201-202.
Search Report with Written Opinion corresponding to Singapore Patent Application No. 11201402660Y, completed May 22, 2015.
Supplementary European Search Report corresponding to European Patent Application No. 12859684, dated May 27, 2015.
Taylor et al. (Mar. 3, 2011) "A Brain-Permeable Small Molecule Reduces Neuronal Cholesterol by Inhibiting Activity of Sirtuin 2 Deacetylase," ACS Chemical Biology. 6:540-546.
The Merck Index (2013) "Infliximab," An Encyclopedia of Chemicals, Drugs and Biologicals. 14th Ed. p. 924.

(56) References Cited

OTHER PUBLICATIONS

International Search Report and Written Opinion for International Application No. PCT/IB2019/000231, dated Jul. 19, 2019.
Lahlali, T., et al., "Novel Potent Capsid Assembly Modulators Regulate Multiple Steps of the Hepatitis B Virus Life Cycle", Antimicrobial Agents and Chemotherapy, Oct. 2018, pp. 1-15, vol. 62, Issue 10.
(Jun. 7, 2012) "Chemical Abstract Registry No. 1375909-37-7", Indexed in the Registry File on STN CAS Online.
(Dec. 28, 2008) "Database Registry (Online) Chemical Abstracts Service", Database Accession No. 1090750-88-1, XP002762544.
(Dec. 22, 2008) "Database Registry [Online] Chemical Abstracts Service", Abstract, Database Accession No. 1088200-12-7, XP002720955.
ASLNEX, Chemical Library; Registry No. 919040-37-2; 0210212007, (2007).
Basarab, et al. (Aug. 15, 2008) "Design of Helicobacter pylori Glutamate Racemase Inhibitors as Selective Antibacterial Agents: A Novel Pro-Drug Approach to Increase Exposure", Bioorganic & Medicinal Chemistry Letters, vol. 18, No. 16, pp. 4716-4722.
Bing, et al. (2009) "Progress in Anti Hepatitis B Virus Non-Nucleosidic Drugs", J. Liaoning Medical University, vol. 30, No. 1, pp. 88-91.
Campagna, et al. (Oct. 9-12, 2011) "Sulfamoylbenzamide Derivatives are a Novel Class of Hepatitis B Virus Inhibitors Targeting PGRNA Encapsidation", International Meeting on Molecular Biology of Hepatitis B Viruses, Poster Presentation, 1 Page.
Carver, et al. (1997) "Polyfunctionalisation of Imidazole via Sequential Imidazolyl Anion Formation", Tetrahedron, vol. 53, Issue 42, pp. 14481-14496.
Chavan, et al. (Oct. 18, 2018) "Cellulose Based Polymers in Development of Amorphous Solid Dispersions, Asian Journal of Pharmaceutical Sciences", vol. 14, No. 3, pp. 248-264.
Chemdiv, Inc. "1 H-Pyrazole-4-Carboxamide, 1-Ethyl-N-phenyl-3-(4-Thiornorpholinyiaulfonyl1)—(CA Index Name)", CHEMCATS, Mar. 2, 2012, RN 1359596-55-6 Registry, 1 Page.
Chemdiv, Inc. "1 H-PyraZole-4-carboxarnide, N-( 4-fluoro-3-methyipllenyl)-3-(llexallydro-1 Hazepin-1-y1) sulfonyl1]-1-methyl—(CA Index Name)", CHEMCATS, Mar. 2, 2012, RN 1359583-56-4 Registry, 1 Page.
Extended European Search Report received for European Application No. 16180180.8, dated Oct. 19, 2016, 8 Pages.
Foley, Louise H. (1994) "An Efficient Synthesis of 2-Chloro-3-Carboethoxy-or 2-Chloro-3-Cyano-4, 5-Disubstituted and 5-Substituted Pyrroles", Tetrahedron letters vol. 35, No. 33, pp. 5989-5992.
Friesen, et al. (Dec. 1, 2008) "Hydroxypropyl Methylcellulose Acetate Succinate-Based Spray-Dried Dispersions: An Overview", Molecular Pharmaceutics, vol. 5, No. 6, pp. 1003-1019.
Geng, et al. (Apr. 1, 2013) "Small-Molecule Inhibitors for the Treatment of Hepatitis B Virus Documented in Patents", Mini reviews in Medicinal Chemistry, vol. 13, No. 5, (XP055105561-XP009176654), pp. 749-776.
Goodman, et al. (2009) "Discovery of Potent, Selective Sulfonylfuran Urea Endothelial Lipase Inhibitors", Bioorganic & Medicinal Chemistry Letters, vol. 19, No. 1, pp. 27-30.
Hughes, et al. (Jul. 2, 2011) "Hepatitis Delta Virus", The Lancet, vol. 378, No. 9785, pp. 73-85.
Jayathilaka, et al. (Oct. 14, 2008) "A Chemical Compound that Stimulates the Human Homologous Recombination Protein RAD51", Proceedings of the National Academy of Sciences on the United States of America, vol. 105, No. 41, pp. 15848-15853.
Liu et al. (Mar. 1, 2012) "Discovery of Highly Potent and Selective Pan-Aurora Kinase Inhibitors with Enhanced in Vivo antitumor Therapeutic Index", Journal of Medicinal chemistry, vol. 55, No. 07, pp. 3250-3260.
Moranta, et al. (1998) "Synthesis and Properties of 1-Alkyl-2-Methyl-3-Sulfonylpyrroles and 1-Alkyl-2-Methyl-3-Sulfonylpyrrole-5-carboxylic Acid Derivatives", Journal of the Chemical Society, Perkin Transactions, vol. 19, pp. 3285-3292.

Nijampatnam, et al. (Jun. 2019) "Recent Advances in the Development of HBV Capsid Assembly Modulators", Current Opinion in Chemical Biology, vol. 50, pp. 73-79.
Online Registry Via STN Feb. 2, 2007, RN 919040-55-4.
Online Registry Via STN, Feb. 2, 2007, RN 919040-48-5.
Online Registry Via STN, Feb. 2, 2007, RN 919040-39-4.
Online Registry Via STN, Feb. 2, 2007, RN 919040-53-2.
Online Registry Via STN, Feb. 3, 2007, RN 924514-21-6.
Online Registry Via STN, Feb. 9, 2003, RN 577752-12-6.
Online Registry Via STN, Jun. 8, 2012, RN 1386725-02-5.
Online Registry Via STN, Jun. 9, 2011, RN 1328738-57-3.
Online Registry Via STN, Aug. 12, 2012, RN 1389720-57-3.
Online Registry Via STN, Aug. 24, 2019, RN 1275589-30-4.
Online Registry via STN, Aug. 24, 2019, RN 311800-19-8.
Online Registry via STN, Aug. 24, 2019, RN 312756-74-4.
Online Registry via STN, Aug. 24, 2019, RN 312756-75-5.
Online Registry via STN, Aug. 24, 2019, RN 313225_30_8.
Online Registry via STN, Aug. 24, 2019, RN 313254-27-2.
Online Registry Via STN, Sep. 1, 2001, RN 313253-89-3.
Online Registry Via STN, Oct. 10, 2001, RN 361373-90-2.
Online Registry Via STN, Nov. 12, 2007, RN 957487-45-5.
Online Registry Via STN, Nov. 12, 2007, RN 957487-49-9.
Online Registry Via STN, Dec. 8, 2012, RN 1389686-79-6.
Online Registry Via STN, Aug. 13, 2012, RN 1390500-09-0.
Online Registry Via STN, Aug. 13, 2012, RN 1390589-54-4.
Online Registry Via STN, Feb. 15, 2007, RN 921179-95-5.
Online Registry Via STN, Jan. 16, 2001, RN 314043-17-9.
Online Registry Via STN, Mar. 17, 2003, RN 499189-09-2.
Online Registry Via STN, Mar. 17, 2013, RN 1424462-66-7.
Online Registry Via STN, Sep. 18, 2012, RN 1394742-82-5.
Online Registry Via STN, Apr. 19, 2008, RN 930914-71-9.
Online Registry Via STN, 2010, RN 1253220-91-5.
Online Registry Via STN, Apr. 24, 2002, RN 406926-60-1.
Online Registry via STN, Apr. 28, 2011, RN 1286906-97-5.
Online Registry Via STN, Aug. 30, 2011, RN 1325664-90-1.
Qiu, et al. (Nov. 1, 2013) "Antihepatitis B Therapy: A Review of Current Medications and Novel Small Molecule Inhibitors", Fundamental & Clinical Pharmacology, vol. 28, No. 4, pp. 1-18.
Schroder, et al. (Jan. 1976) "Arzneimittel Chemie Passage", Arzneimittelchemie Grundlagen Nerven, 8 Pages (4 Pages of English Translation and 4 Pages of Original Copy).
Stalder, et al. (Dec. 21, 2010) "Selective Antagonists of Mouse Trace Amine-Associated Receptor 1 (mTAAR1): Discovery of EPPTB (RO5212773)", Bioorganic & Medicinal Chemistry Letters, vol. 21, pp. 1227-1231.
Wang, et al. (2009) "Synthesis and Evaluation of Benzothiazole-Based Analogues as Novel, Potent, and Selective Fatty Acid Amide Hydrolase Inhibitors", Journal of Medicinal Chemistry, vol. 52, No. 1, pp. 170-180.
Watanabe, et al. (Oct. 30, 1968) "Ortho Lithiation of N, N-dimethylbenzenesulfonamide by N-butyllithium. Condensation with electrophilic compounds", Canadian Journal of Chemistry, vol. 47, No. 9, pp. 1543-1546.
Online Registry via STN Oct. 10, 1987, RN 110644-97-8.
Online Registry via STN Jul. 16, 1992, RN 142428-99-7.
Online Registry via STN Mar. 18, 2010, RN 1211415-65-4.
Chemical Abstract (CAS) Registry No. 1211415-65-4, Indexed in the Registry File on STN CAS Online, Mar. 18, 2010.
Chen, et al., "Entecavir vs. Lamivudine in Chronic Hepatitis B Patients with Severe Acute Exacerbation and Hepatic Decompensation", Journal of Hepatology, 2014, vol. 60, pp. 1127-1134.
Extended European Search Report Received for EP Patent Application No. 13189880.1, dated Mar. 17, 2014, 3 pages.
Extended European Search Report Received for EP Patent Application No. 15175021.3, dated Aug. 12, 2015, 4 pages.
International Preliminary Report on Patentability received for PCT Application No. PCT/EP2013/072690, dated May 12, 2015, 6 pages.
International Search Report and Written Opinion received for PCT Patent Application No. PCT/EP2016/065488, dated Aug. 10, 2016, 8 pages.

(56) References Cited

OTHER PUBLICATIONS

Klumpp, et al., "High Antiviral Activity of the HBV Core Inhibitor NVR 3-778 in the Humanized uPA/SCID Mouse Model", Journal of Hepatology, 2015, vol. 62, p. S235.

* cited by examiner

CAPSID ASSEMBLY MODULATOR DOSING REGIMEN

CROSS-REFERENCE TO RELATED APPLICATION

This application claims priority to U.S. Provisional Application No. 62/642,997 filed on Mar. 14, 2018, which is incorporated herein in its entirety.

BACKGROUND

Chronic hepatitis B virus (HBV) infection is a persistent, potentially progressive necroinflammatory liver disease associated with chronic HBV infection. Worldwide about 240-400 million persons are chronically infected with HBV, and chronic HBV infection is a major global cause of severe liver morbidity and liver-related mortality (Hepatitis B Factsheet, World Health Organization, 2013; Hoofnagle J H, et al., Management of Hepatitis B: Summary of a Clinical Research Workshop, Hepatology, 2007, 45(4):1056-1075; EASL Clinical Practice Guidelines: Management of chronic hepatitis B virus infection, J. Hepatology, 2012, 57:167-185 (EASL 2012); Lesmana L A, et al. Hepatitis B: overview of the burden of disease in the Asia-Pacific region, Liver International, 2006, 26:3-10; Lok ASF and McMahon B J, Chronic Hepatitis B: Update 2009, Hepatology, September 2009:1-36 (Lok 2009)).

With the continued worldwide prevalence of HBV-associated mortality and severe morbidity, there remains a need for improved HBV antiviral therapies that can achieve sustained viral response during and after treatment.

SUMMARY

The present disclosure is directed to methods of using a capsid assembly inhibitor for the treatment of hepatitis B virus infection. In an aspect, provided herein is a method of preventing or treating HBV infection in a subject, said method comprising administering to said subject a Compound of Formula 1:

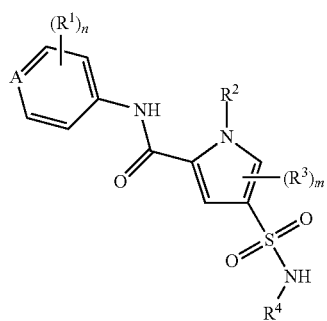

(1)

or a pharmaceutically acceptable salt thereof,
wherein:
A is N or CH;
$R^1$ is, independently at each occurrence, selected from halo, $CF_3$, and CN;
$R^2$ is $C_1$-$C_3$ alkyl;
$R^3$ is, independently at each occurrence, selected from $C_1$-$C_3$ alkyl and halo;
$R^4$ is $C_1$-$C_4$ alkyl, which is independently substituted 1 or 2 times with halo or $CF_3$;
n is 0, 1, 2, or 3; and
m is 0, 1, or 2;
at a daily dose of 50-500 mg wherein a Compound of Formula 1 is administered in at least one dosage form having a formulation comprising a stabilizer.

In some embodiments, the Compound of Formula I is Compound A:

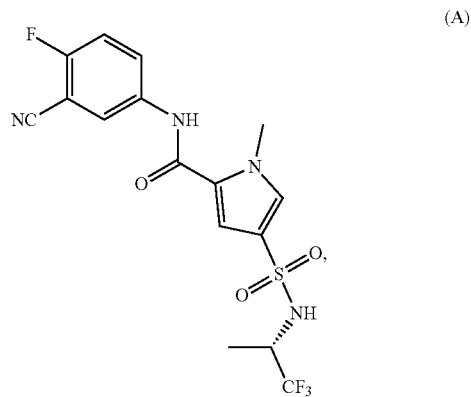 [SMILES: C[C@H](NS(=O)(=O)c1cc(C(=O)Nc2ccc(F)c(C#N)c2)n(C)c1)C(F)(F)F]

(A)

or a pharmaceutically acceptable salt thereof.

In other embodiments, the Compound of Formula I is Compound B:

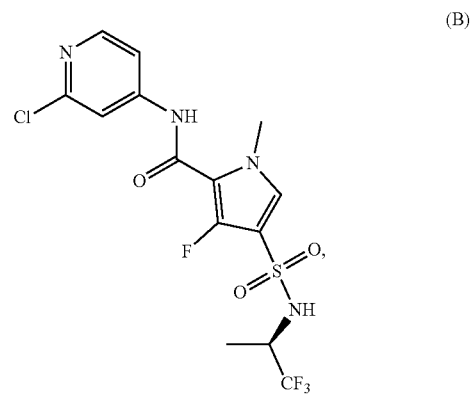 [SMILES: C[C@@H](NS(=O)(=O)c1cn(C)c(C(=O)Nc2ccnc(Cl)c2)c1F)C(F)(F)F]

(B)

or a pharmaceutically acceptable salt thereof,

In an embodiment of the method, the daily dose is 75-250 mg.

In another embodiment of the method, the daily dose is 250 mg.

In still another embodiment of the method, the stabilizer is at least one of Hypromellose (HPMC) and Hypromellose acetate succinate (HPMC-AS). Hypromellose (HPMC) may e.g., be HPMC E5 (i.e., HPMC with a viscosity of 5 mPa·s).

In an embodiment of the method, the amount of a Compound of Formula 1 and the amount of stabilizer are present in the dosage form at a ratio of 1:1 by weight. In another embodiment of the method, the amount of a Compound of Formula 1 and the amount of stabilizer are present in the dosage form at a ratio of 1:2 by weight. In another embodiment of the method, the amount of a Compound of Formula 1 and the amount of stabilizer are present in the dosage form at a ratio of 1:3 by weight. In another embodiment of the method, the amount of a Compound of Formula 1 and the amount of stabilizer are present in the dosage form at a ratio of 1:4 by weight. In yet another embodiment of the method, the amount of a Compound of Formula 1 and the amount of stabilizer are present in the dosage form at a ratio of 1:5 by weight.

In an embodiment of the method, a Compound of Formula 1 is administered in a single dosage form.

In an embodiment of the method, a Compound of Formula 1 is administered to prevent HBV infection in the subject.

In an embodiment of the method, the method further comprises administering a transcription inhibitor to the subject. In an embodiment of the method, transcription inhibitor is a nucleoside analog. In an embodiment of the method, the nucleoside analog is tenofovir, or a pharmaceutically acceptable salt or prodrug thereof, tenofovir alafenamide, or a pharmaceutically acceptable salt or prodrug thereof, or entecavir, or a pharmaceutically acceptable salt thereof. In an embodiment of the method, the nucleoside analog is tenofovir disoproxil fumarate or entecavir monohydrate. In an embodiment of the method, the nucleoside analog is tenofovir disoproxil fumarate. In an embodiment of the method, the nucleoside analog is entecavir monohydrate.

In an embodiment of the method, the tenofovir disoproxil fumarate is administered in an amount of 60-600 mg. In another embodiment of the method, the tenofovir disoproxil fumarate is administered in an amount of 300 mg. In yet another embodiment of the method, the entecavir monohydrate is administered in an amount of 0.1-1 mg. In still another embodiment of the method, the entecavir monohydrate is administered in an amount of 0.5 mg.

In an embodiment of the method, the method further comprises administering an immune modulator. In an embodiment of the method, the immune modulator is interferon, for example interferon alpha or pegylated interferon alpha. In an embodiment of the method, the subject is treatment naïve.

In some embodiments, the method further comprises administering at least one Nucleic Acid Polymer (NAP), more particularly at least one NAP which inhibits the release of subviral particles from hepatocytes.

In some embodiments, the method further comprises administering at least one short interfering RNA (siRNA) or antisense oligonucleotide (ASO), more particularly at least one siRNA or ASO selected from the group of siRNAs and ASOs which inhibit the expression of one or more genes that are necessary for replication or pathogenesis of HBV.

In another aspect, provided herein is a pharmaceutical composition comprising a Compound of Formula 1 in an amount of 50-500 mg. In an embodiment of the pharmaceutical composition, the composition further comprises 50-1500 mg stabilizer. In an embodiment of the pharmaceutical composition, the amount of a Compound of Formula 1 is 75-250 mg. In an embodiment of the pharmaceutical composition, the amount of a Compound of Formula 1 is 250 mg.

The pharmaceutical composition can comprise at least one polymer chosen from among HPMC-AS and HPMC E5, and wherein said at least one polymer is in an amount of 50-1500 mg. In an embodiment, at least one dosage form of the pharmaceutical composition comprises at least one polymer chosen from among HPMC (for example HPMC E5) and HPMC AS.

In another aspect, provided herein is a method of decreasing formation of HBV cccDNA in a subject infected with HBV or at risk of being infected with HBV, said method comprising administering to said subject a Compound of Formula 1 at a daily dose of 50-500 mg wherein a Compound of Formula 1 is administered in at least one dosage form having a formulation comprising a stabilizer.

In another aspect, provided herein is a method of decreasing HBsAg in a subject infected with HBV or at risk of being infected with HBV, said method comprising administering to said subject a Compound of Formula 1 at a daily dose of 50-500 mg wherein a Compound of Formula 1 is administered in at least one dosage form having a formulation comprising a stabilizer.

In yet another aspect, provided herein is a method of preventing HBV infection in a subject at risk of being infected with HBV by decreasing formation of HBV cccDNA, said method comprising administering to said subject a Compound of Formula 1 at a daily dose of 50-500 mg wherein a Compound of Formula 1 is administered in at least one dosage form having a formulation comprising a stabilizer.

In various embodiments of the methods provided herein, the method further comprises administering a nucleos(t)ide analogue.

DETAILED DESCRIPTION

Figure 1:
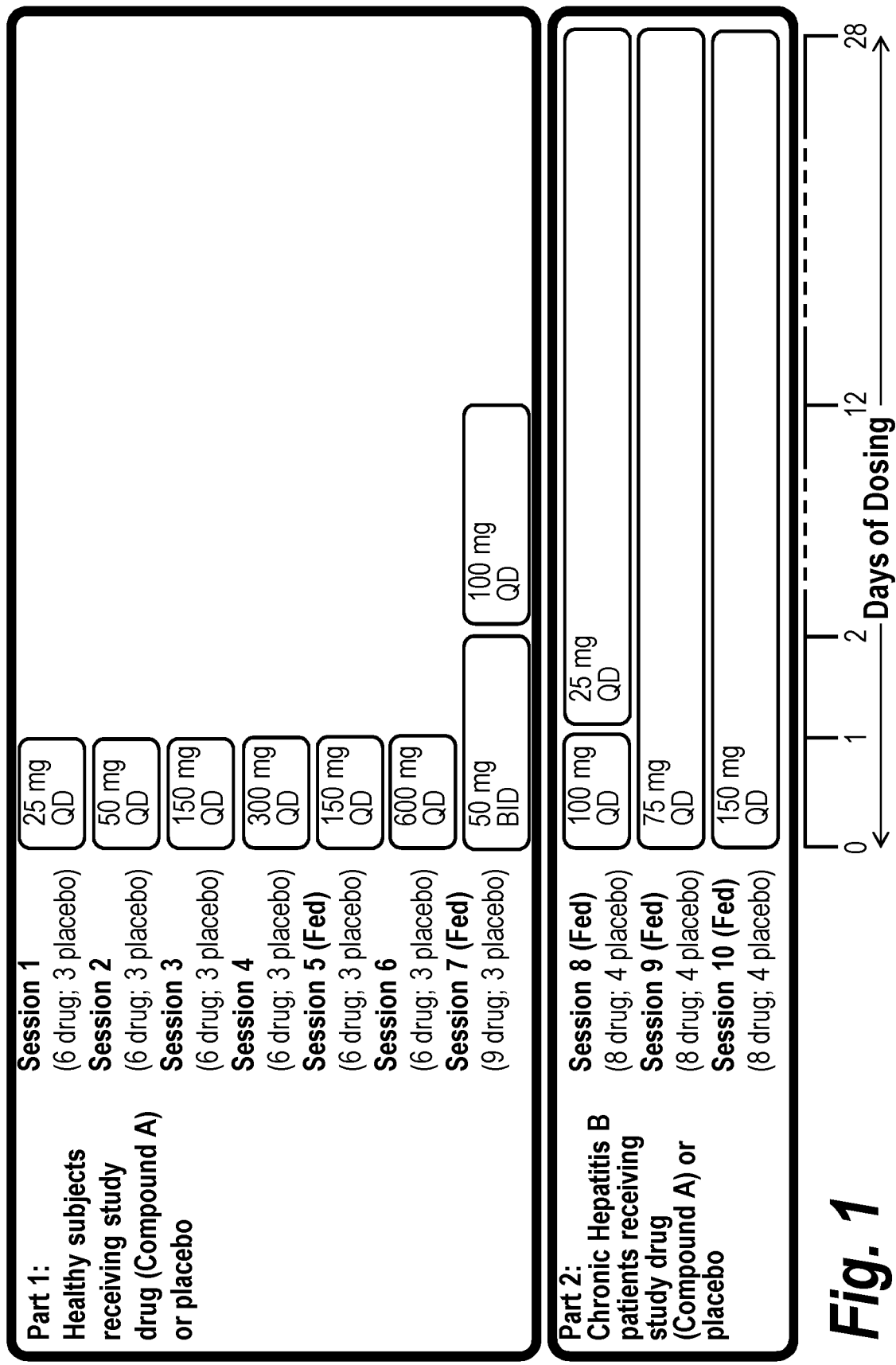
FIG. 1 depicts the study design for the First-In-Human study of Compound A in healthy patients and patients with chronic HBV.

The present disclosure is directed to methods of using a capsid assembly inhibitor for the treatment of hepatitis B virus infection. It has now been found that administration of capsid assembly modulators (CAMs) can interfere with HBV capsid assembly, which is a key step in virus production, and are therefore an attractive new area of development. Unexpectedly, it has been found that administration of a Compound of Formula 1 to a patient with chronic HBV infection may result in reduction of HBsAg, HBeAg or induce seroconversion in that patient. More particularly, such results can be achieved through administration to the patient of a safe and therapeutically effective dose of a Compound of Formula 1 such as a daily dose of 50-500 mg of a Compound of Formula 1.

Definitions

As used in the specification and in the claims, the term "comprising" can include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated compounds, which allows the presence of only the named compounds, along with any pharmaceutically acceptable carriers, and excludes other compounds.

All ranges disclosed herein are inclusive of the recited endpoint and independently combinable (for example, the range of "from 50 mg to 500 mg" is inclusive of the endpoints, 50 mg and 500 mg, and all the intermediate values). The endpoints of the ranges and any values disclosed herein are not limited to the precise range or value; they are sufficiently imprecise to include values approximating these ranges and/or values.

As used herein, approximating language can be applied to modify any quantitative representation that can vary without resulting in a change in the basic function to which it is related. Accordingly, a value modified by a term or terms, such as "about" and "substantially," cannot be limited to the precise value specified, in some cases. In at least some instances, the approximating language can correspond to the precision of an instrument for measuring the value. The modifier "about" should also be considered as disclosing the range defined by the absolute values of the two endpoints. For example, the expression "from about 50 to about 500" also discloses the range "from 50 to 500." The term "about" can refer to plus or minus 10% of the indicated number. For example, "about 10%" can indicate a range of 9% to 11%, and "about 1" can mean, from 0.9 to 1.1. Other meanings of "about" can be apparent from the context, such as rounding off, so, for example "about 1" can also mean from 0.5 to 1.4.

As used herein, the term "treatment" or "treating," is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has HBV infection, chronic HBV infection, a symptom of HBV infection or the potential to develop HBV infection, with the purpose to cure, heal, alleviate, relieve, alter, remedy, ameliorate, improve or affect HBV infection, the symptoms of HBV infection or the potential to develop HBV infection. Such treatments can be specifically tailored or modified, based on knowledge obtained from the field of pharmacogenomics.

The term "prevent," "preventing," or "prevention" as used herein comprises the prevention of at least one symptom associated with or caused by the state, disease or disorder being prevented.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject or individual is human.

As used herein, the term "pharmaceutically acceptable" refers to a material, such as a carrier or diluent, which does not abrogate the biological activity or properties of the compound, and is relatively non-toxic, i.e., the material can be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it can perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that can serve as pharmaceutically acceptable carriers include; sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention and are physiologically acceptable to the patient. Supplementary active compounds can also be incorporated into the compositions. The "pharmaceutically acceptable carrier" can further include a pharmaceutically acceptable salt of the compound useful within the invention. Other additional ingredients that can be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

The term "stabilizer," as used herein, refers to polymers capable of chemically inhibiting or preventing degradation of a Compound of Formula 1. Stabilizers are added to formulations of compounds to improve chemical and physical stability of the compound.

The term "combination," "therapeutic combination," "pharmaceutical combination," or "combination product" as used herein refer to a non-fixed combination or a kit of parts for the combined administration where two or more therapeutic agents can be administered independently, at the same time or separately within time intervals, especially where these time intervals allow that the combination partners show a cooperative, e.g., synergistic, effect.

As used herein, "treatment naïve" refers to a patient not having previously received treatment with a drug, investigational or approved, for HBV infection, in particular a nucleos(t)ide drug. "Treatment naïve" also refers to a patient not having been on treatment with HBV antiviral medicines within six months of entering a clinical study.

Alternatively, patients treated according to the methods of the disclosure can be "treatment experienced." As used herein, "treatment experienced" refers to a patient who has had at least one previous course of an HBV antiviral therapy, in particular a nucleos(t)ide drug. In some embodiments, the last dose in this previous course occurred at least three months prior to implementing a method according to the present disclosure.

HBV infections that may be treated according to the disclosed methods include HBV genotype A, B, C, and/or D infections. However, in an embodiment, the methods disclosed may treat any HBV genotype ("pan-genotypic treatment"). HBV genotyping may be performed using methods known in the art, for example, INNO-LIPA® HBV Genotyping, Innogenetics N.V., Ghent, Belgium).

The term "synergistic effect" refers to the action of two agents, such as, for example, a capsid assembly modulator and a nucleos(t)ide analogue, producing an effect, for example, slowing the symptomatic progression of HBV-infection or symptoms thereof, which is greater than the simple addition of the effects of each drug administered alone. A synergistic effect can be calculated, for example, using suitable methods such as the Sigmoid-Emax equation (Holford, N. H. G. and Scheiner, L. B., Cline Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984) and Chou, Pharmacol, Rev. 58: 621-681 (2006). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively. In some embodiments, the combination of compounds exhibits a synergistic effect (i.e., greater than additive effect) in the treatment of HBV infection.

Synergy volumes of <−100, −100 to −50, −50 to −25, −25 to 25, 25 to 50, 50 to 100, and >100 indicate strong antagonism, moderate antagonism, slight antagonism, insignificant synergism/antagonism (additivity), slight synergism, moderate synergism, and strong synergism respectively.

Synergy can be defined as an improvement in any beneficial effect of each of a Compound of Formula 1 or a nucleos(t)ide analogue, alone or in combination. The improvement may exceed an additive effect of the combination or may only occur as a result of the combination. For example, in an embodiment, the effect is complete or sustained reduction of viral load, HBsAg and/or anti-HBsAb during and/or after treatment. For example, in an embodiment, the effect is sustained virological response (SVR) and/or sustained viral clearance.

Dosing/Administration

In one aspect, the present disclosure is directed to methods of treating HBV infection in a patient in need thereof, comprising administering to the patient a Compound of the Formula 1:

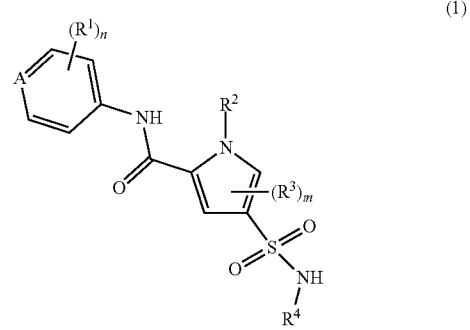

or a pharmaceutically acceptable salt thereof,
wherein:
A is N or CH;
$R^1$ is, independently at each occurrence, selected from halo, $CF_3$, and CN;
$R^2$ is $C_1$-$C_3$ alkyl;
$R^3$ is, independently at each occurrence, selected from $C_1$-$C_3$ alkyl and halo;
$R^4$ is $C_1$-$C_4$ alkyl, which is independently substituted 1 or 2 times with halo or $CF_3$;
n is 0, 1, 2, or 3; and
m is 0, 1, or 2.

In some embodiments, the amount of a Compound of Formula 1 is from about 50 mg per day to about 500 mg per day (e.g. 50, 75, 100, 150, 200, 250, 300, 350, 400, 450, 500 mg). In some embodiments, the amount of a Compound of Formula 1 is from 75 mg per day to 250 mg per day. In some embodiments, the amount of a Compound of Formula 1 is 75 mg per day. In some embodiments, the amount of a Compound of Formula 1 is 150 mg per day. In some embodiments, the amount of a Compound of Formula 1 is 250 mg per day.

In some embodiments, the dose or daily dose of the Compound of Formula 1, more particularly of compound (A) or (B), is 5-300 mg, more particularly 25-300 mg, more particularly 50-300 mg, more particularly 75-300 mg, more particularly 80-300 mg, more particularly 100-300 mg, more particularly 100-250 mg.

In some embodiments, the dose or daily dose of the Compound of Formula 1, more particularly of compound (A) or (B), is 5-250 mg, more particularly 25-250 mg, more particularly 50-250 mg, more particularly 75-250 mg, more particularly 80-250 mg, more particularly 100-250 mg.

In some embodiments, the dose or daily dose of the Compound of Formula 1, more particularly of compound (A) or (B), is 50-300 mg, more particularly 75-250 mg, more particularly 100-250 mg.

In an embodiment of the methods of treating HBV infection in a patient in need thereof provided herein, the Compound of Formula 1 is the following compound:

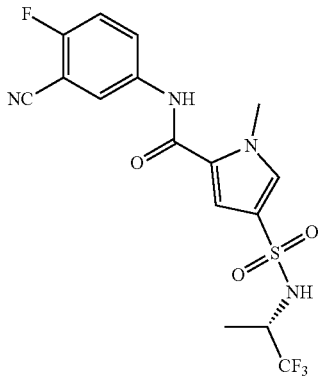

(A)

or a pharmaceutically acceptable salt thereof (hereinafter "Compound A"), in an amount from about 50 mg per day to about 500 mg per day (e.g. 50, 75, 100, 150, 200, 250, 300, 350, 400, 450, 500 mg). In some embodiments, the amount of Compound A is from 75 mg per day to 250 mg per day. In some embodiments, the amount of Compound A is 75 mg per day. In some embodiments, the amount of Compound A is 150 mg per day. In some embodiments, the amount of Compound A is 250 mg per day.

Compound A, including the synthesis thereof, is disclosed in PCT Publication No. WO/2014/184350 (or the US counterparts thereof), which is hereby incorporated by reference in its entirety.

In another embodiment of the methods of treating HBV infection in a patient in need thereof provided herein, the Compound of Formula 1 is the following compound:

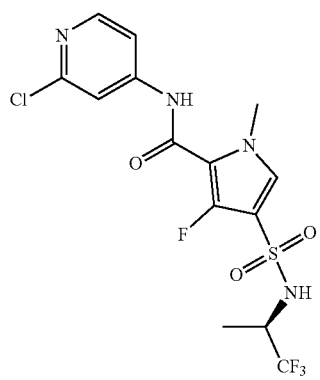

(B)

or a pharmaceutically acceptable salt thereof (hereinafter "Compound B"), in an amount from about 50 mg per day to about 500 mg per day (e.g. 50, 75, 100, 150, 200, 250, 300, 350, 400, 450, 500 mg). In some embodiments, the amount of Compound B is from 75 mg per day to 250 mg per day. In some embodiments, the amount of Compound B is 75 mg per day. In some embodiments, the amount of Compound B is 150 mg per day. In some embodiments, the amount of Compound B is 250 mg per day.

Compound B, including the synthesis thereof, is disclosed in PCT Publication No. WO/2015/118057 (or the US counterparts thereof), which is hereby incorporated by reference in its entirety.

The method of the present disclosure aims at reducing serum HBV DNA, serum HBV RNA, and quantitative serum HBsAg and HBeAg in patients. The methods of treating HBV infection provided herein, in particular, treat HBV infection by reducing serum HBV DNA in a patient, by reducing serum HBV RNA in a patient and/or by reducing serum HBsAg and HBeAg in a patient and/or by inducing seroconversion (against sAg and/or eAg) in a patient.

In certain embodiments of the methods of treating HBV infection provided herein, the treatment is curative and the patient does not have to continue treatment after the specified treatment time. In a particular embodiment of the method of treating HBV provided herein, the treatment is finite.

The present disclosure provides methods of treating HBV infection in a patient in need thereof, comprising administering to the patient a Compound of Formula 1, or a pharmaceutically acceptable salt thereof, in an amount from 50 mg per day to 500 mg per day, wherein a Compound of Formula 1 is administered once per day. In embodiments, the patient is administered a Compound of Formula 1 for a duration of 28 days. In some embodiments, the amount of a Compound of Formula 1 administered to the patient is from 75 mg per day to 250 mg per day. In some embodiments, the amount of a Compound of Formula 1 administered to the patient is 75 mg per day. In some embodiments, the amount of a Compound of Formula 1, or a pharmaceutically acceptable salt thereof, is 150 mg per day. In a particular embodiment, the amount of a Compound of Formula 1 administered to the patient is 250 mg per day.

In an alternative embodiment, the present disclosure provides methods of preventing HBV infection in a patient at risk of being infected with HBV, comprising administering to the patient a Compound of Formula 1, or a pharmaceutically acceptable salt thereof, in an amount from 50 mg per day to 500 mg per day, wherein a Compound of Formula 1 is administered once per day. Thus, in a particular embodiment, the present disclosure provides methods of preventing HBV infection in a patient at risk of being infected with HBV, comprising administering to the patient a Compound of Formula 1, or a pharmaceutically acceptable salt thereof, in an amount of 250 mg per day.

In some embodiments, the methods further comprise administering an immune modulator, such as interferon. In some embodiments, the subject is treatment naïve.

In some embodiments, the methods further comprise administering at least one Nucleic Acid Polymer (NAP), more particularly at least one NAP which inhibits the release of subviral particles from hepatocytes.

In some embodiments, the method further comprises administering at least one short interfering RNA (siRNA) or antisense oligonucleotide (ASO), more particularly at least one siRNA or ASO selected from the group of siRNAs and ASOs which inhibit the expression of one or more genes that are necessary for replication or pathogenesis of HBV.

In some embodiments of the methods, a Compound of Formula 1 is co-administered with a transcription inhibitor. In some embodiments, the transcription inhibitor is a nucleos(t)ide analogue. In some embodiments, the nucleos(t)ide inhibitor is tenofovir or a pharmaceutically acceptable salt thereof or a prodrug thereof (such as tenofovir disoproxil fumarate (TDF), tenofovir alafenamide (TAF), or a pharmaceutically acceptable salt thereof), or entecavir or a pharmaceutically acceptable salt thereof. In some embodiments, a Compound of Formula 1 is co-administered with tenofovir disoproxil fumarate. In some embodiments, a Compound of Formula 1 is co-administered with tenofovir alafenamide. In still other embodiments, a Compound of Formula 1 is co-administered with entecavir monohydrate.

In another embodiment, the present disclosure provides methods of treating HBV infection in a patient in need thereof, comprising administering to the patient a Compound of Formula 1, or a pharmaceutically acceptable salt thereof, in an amount from 50 mg per day to 500 mg per day, and a transcription inhibitor.

In another embodiment, the present disclosure provides methods of treating HBV infection in a patient in need thereof, comprising administering to the patient a Compound of Formula 1, or a pharmaceutically acceptable salt thereof, in an amount from 50 mg per day to 500 mg per day, and a nucleos(t)ide analogue.

In another embodiment, the present disclosure provides methods of treating HBV infection in a patient in need thereof, comprising administering to the patient a Compound of Formula 1, or a pharmaceutically acceptable salt thereof, in an amount from 50 mg per day to 500 mg per day, and tenofovir, or a pharmaceutically acceptable salt, or prodrug thereof, in an amount from 60 mg per day to 600 mg per day.

In some embodiments, the present disclosure provides methods of treating HBV infection in a patient in need thereof, comprising administering to the patient a Compound of Formula 1, or a pharmaceutically acceptable salt thereof, in an amount from 50 mg per day to 500 mg per day, and tenofovir alafenamide, or a pharmaceutically acceptable salt thereof, in an amount from 60 mg per day to 600 mg per day.

In another embodiment, the present disclosure provides methods of treating HBV infection in a patient in need thereof, comprising administering to the patient a Compound of Formula 1, or a pharmaceutically acceptable salt thereof, in an amount from 50 mg per day to 500 mg per day, and entecavir, or a pharmaceutically acceptable salt, in an amount from 0.1 mg per day to 1 mg per day.

In another embodiment, the present disclosure provides methods of treating HBV infection in a patient in need thereof, comprising administering to the patient a Compound of Formula 1, or a pharmaceutically acceptable salt thereof, in an amount from 75 mg per day to 250 mg per day, and tenofovir, or a pharmaceutically acceptable salt or prodrug thereof, in an amount of 300 mg per day. In an embodiment, the co-administration of a Compound of Formula 1, or a pharmaceutically acceptable salt thereof, and tenofovir, or a pharmaceutically acceptable salt or prodrug thereof, produces a synergistic effect.

In some embodiments, the present disclosure provides methods of treating HBV infection in a patient in need thereof, comprising administering to the patient a Compound of Formula 1 or a pharmaceutically acceptable salt thereof in an amount from 75 mg per day to 250 mg per day, and tenofovir alafenamide or a pharmaceutically acceptable salt thereof in an amount of 300 mg per day. In an embodiment, the co-administration of a Compound of Formula 1 or a pharmaceutically acceptable salt thereof, and tenofovir alafenamide or a pharmaceutically acceptable salt thereof, produces a synergistic effect.

In another embodiment, the present disclosure provides methods of treating HBV infection in a patient in need thereof, comprising administering to the patient a Compound of Formula 1, or a pharmaceutically acceptable salt thereof, in an amount from 75 mg per day to 250 mg per day, and entecavir, or a pharmaceutically acceptable salt, in an amount of 0.5 mg per day. In an embodiment, the co-administration of a Compound of Formula 1, or a pharmaceutically acceptable salt thereof, and entecavir, or a pharmaceutically acceptable salt, produces a synergistic effect.

In another embodiment, the present disclosure provides methods of treating HBV infection in a patient in need thereof, comprising administering to the patient a Compound of Formula 1, or a pharmaceutically acceptable salt thereof, in an amount of 250 mg per day, and tenofovir, or a pharmaceutically acceptable salt, or prodrug thereof, in an amount of 300 mg per day.

In some embodiments, the present disclosure provides methods of treating HBV infection in a patient in need thereof, comprising administering to the patient a Compound of Formula 1, or a pharmaceutically acceptable salt thereof, in an amount of 250 mg per day, and tenofovir alafenamide, or a pharmaceutically acceptable salt thereof, in an amount of 300 mg per day.

In another embodiment, the present disclosure provides methods of treating HBV infection in a patient in need thereof, comprising administering to the patient a Compound of Formula 1, or a pharmaceutically acceptable salt thereof, in an amount of 250 mg per day, and entecavir, or a pharmaceutically acceptable salt, in an amount of 0.5 mg per day.

Also provided herein are methods of treating HBV infection in a patient in need thereof, comprising administering to the patient Compound A, or a pharmaceutically acceptable salt thereof, in an amount from 50 mg per day to 500 mg per day, wherein Compound A is administered once per day. In embodiments, the patient is administered Compound A for a duration of 28 days. In some embodiments, the amount of Compound A administered to the patient is from 75 mg per day to 250 mg per day. In some embodiments, the amount of Compound A administered to the patient is 75 mg per day. In some embodiments, the amount of Compound A, or a pharmaceutically acceptable salt thereof, is 150 mg per day. In a particular embodiment, the amount of Compound A administered to the patient is 250 mg per day.

In an alternative embodiment, the present disclosure provides methods of preventing HBV infection in a patient at risk of being infected with HBV, comprising administering to the patient Compound A, or a pharmaceutically acceptable salt thereof, in an amount from 50 mg per day to 500 mg per day, wherein Compound A is administered once per day. Thus, in a particular embodiment, the present disclosure provides methods of preventing HBV infection in a patient at risk of being infected with HBV, comprising administering to the patient Compound A, or a pharmaceutically acceptable salt thereof, in an amount of 250 mg per day.

In some embodiments of the methods, Compound A is co-administered with a transcription inhibitor. In some embodiments, the transcription inhibitor is a nucleos(t)ide analogue. In some embodiments, the nucleos(t)ide inhibitor is tenofovir or a pharmaceutically acceptable salt thereof or a prodrug thereof (such as tenofovir disoproxil fumarate (TDF), tenofovir alafenamide (TAF), or a pharmaceutically acceptable salt thereof), or entecavir or a pharmaceutically acceptable salt thereof. In some embodiments, Compound A is co-administered with tenofovir disoproxil fumarate. In some embodiments, Compound A is co-administered with tenofovir alafenamide. In other embodiments, Compound A is co-administered with entecavir monohydrate.

In another embodiment, the present disclosure provides methods of treating HBV infection in a patient in need thereof, comprising administering to the patient Compound A, or a pharmaceutically acceptable salt thereof, in an amount from 50 mg per day to 500 mg per day, and a transcription inhibitor.

In another embodiment, the present disclosure provides methods of treating HBV infection in a patient in need thereof, comprising administering to the patient Compound A, or a pharmaceutically acceptable salt thereof, in an amount from 50 mg per day to 500 mg per day, and a nucleos(t)ide analogue.

In another embodiment, the present disclosure provides methods of treating HBV infection in a patient in need thereof, comprising administering to the patient Compound A, or a pharmaceutically acceptable salt thereof, in an amount from 50 mg per day to 500 mg per day, and tenofovir, or a pharmaceutically acceptable salt, or prodrug thereof, in an amount from 60 mg per day to 600 mg per day.

In some embodiments, the present disclosure provides methods of treating HBV infection in a patient in need thereof, comprising administering to the patient Compound A, or a pharmaceutically acceptable salt thereof, in an amount from 50 mg per day to 500 mg per day, and tenofovir alafenamide, or a pharmaceutically acceptable salt thereof, in an amount from 60 mg per day to 600 mg per day.

In another embodiment, the present disclosure provides methods of treating HBV infection in a patient in need thereof, comprising administering to the patient Compound A, or a pharmaceutically acceptable salt thereof, in an amount from 50 mg per day to 500 mg per day, and entecavir, or a pharmaceutically acceptable salt, in an amount from 0.1 mg per day to 1 mg per day.

In another embodiment, the present disclosure provides methods of treating HBV infection in a patient in need thereof, comprising administering to the patient Compound A, or a pharmaceutically acceptable salt thereof, in an amount from 75 mg per day to 250 mg per day, and tenofovir, or a pharmaceutically acceptable salt or prodrug thereof, in an amount of 300 mg per day. In an embodiment, the co-administration of Compound A, or a pharmaceutically acceptable salt thereof, and tenofovir, or a pharmaceutically acceptable salt or prodrug thereof, produces a synergistic effect.

In some embodiments, the present disclosure provides methods of treating HBV infection in a patient in need thereof, comprising administering to the patient Compound A, or a pharmaceutically acceptable salt thereof, in an amount from 75 mg per day to 250 mg per day, and tenofovir alafenamide, or a pharmaceutically acceptable salt thereof, in an amount of 300 mg per day. In an embodiment, the co-administration of Compound A, or a pharmaceutically acceptable salt thereof, and tenofovir alafenamide, or a pharmaceutically acceptable salt thereof, produces a synergistic effect.

In another embodiment, the present disclosure provides methods of treating HBV infection in a patient in need thereof, comprising administering to the patient Compound A, or a pharmaceutically acceptable salt thereof, in an amount from 75 mg per day to 250 mg per day, and entecavir, or a pharmaceutically acceptable salt, in an amount of 0.5 mg per day. In an embodiment, the co-administration of Compound A, or a pharmaceutically acceptable salt thereof, and entecavir, or a pharmaceutically acceptable salt, produces a synergistic effect.

In another embodiment, the present disclosure provides methods of treating HBV infection in a patient in need thereof, comprising administering to the patient Compound A, or a pharmaceutically acceptable salt thereof, in an amount of 250 mg per day, and tenofovir, or a pharmaceutically acceptable salt, or prodrug thereof, in an amount of 300 mg per day.

In some embodiments, the present disclosure provides methods of treating HBV infection in a patient in need thereof, comprising administering to the patient Compound A, or a pharmaceutically acceptable salt thereof, in an amount of 250 mg per day, and tenofovir alafenamide, or a pharmaceutically acceptable salt thereof, in an amount of 300 mg per day.

In another embodiment, the present disclosure provides methods of treating HBV infection in a patient in need thereof, comprising administering to the patient Compound A, or a pharmaceutically acceptable salt thereof, in an amount of 250 mg per day, and entecavir, or a pharmaceutically acceptable salt, in an amount of 0.5 mg per day.

Also provided herein are methods of treating HBV infection in a patient in need thereof, comprising administering to the patient Compound B, or a pharmaceutically acceptable salt thereof, in an amount from 50 mg per day to 500 mg per day, wherein Compound B is administered once per day. In embodiments, the patient is administered Compound B for a duration of 28 days. In some embodiments, the amount of Compound B administered to the patient is from 75 mg per day to 250 mg per day. In some embodiments, the amount of Compound B administered to the patient is 75 mg per day. In some embodiments, the amount of Compound B, or a pharmaceutically acceptable salt thereof, is 150 mg per day. In a particular embodiment, the amount of Compound B administered to the patient is 250 mg per day.

In an alternative embodiment, the present disclosure provides methods of preventing HBV infection in a patient at risk of being infected with HBV, comprising administering to the patient Compound B, or a pharmaceutically acceptable salt thereof, in an amount from 50 mg per day to 500 mg per day, wherein Compound B is administered once per day. Thus, in a particular embodiment, the present disclosure provides methods of preventing HBV infection in a patient at risk of being infected with HBV, comprising administering to the patient Compound B, or a pharmaceutically acceptable salt thereof, in an amount of 250 mg per day.

In some embodiments of the methods, Compound B is co-administered with a transcription inhibitor. In some embodiments, the transcription inhibitor is a nucleos(t)ide analogue. In some embodiments, the nucleos(t)ide inhibitor is tenofovir or a pharmaceutically acceptable salt thereof or a prodrug thereof (such as tenofovir disoproxil fumarate (TDF), tenofovir alafenamide (TAF), or a pharmaceutically acceptable salt thereof), or entecavir, or a pharmaceutically acceptable salt thereof. In some embodiments, Compound B is co-administered with tenofovir disoproxil fumarate. In some embodiments, Compound B is co-administered with tenofovir alafenamide. In other embodiments, Compound B is co-administered with entecavir monohydrate.

In another embodiment, the present disclosure provides methods of treating HBV infection in a patient in need thereof, comprising administering to the patient Compound B, or a pharmaceutically acceptable salt thereof, in an amount from 50 mg per day to 500 mg per day, and a transcription inhibitor.

In another embodiment, the present disclosure provides methods of treating HBV infection in a patient in need thereof, comprising administering to the patient Compound B, or a pharmaceutically acceptable salt thereof, in an amount from 50 mg per day to 500 mg per day, and a nucleos(t)ide analogue.

In another embodiment, the present disclosure provides methods of treating HBV infection in a patient in need thereof, comprising administering to the patient Compound B, or a pharmaceutically acceptable salt thereof, in an amount from 50 mg per day to 500 mg per day, and tenofovir, or a pharmaceutically acceptable salt, or prodrug thereof, in an amount from 60 mg per day to 600 mg per day.

In some embodiments, the disclosure provides methods of treating HBV infection in a patient in need thereof, comprising administering to the patient Compound B, or a pharmaceutically acceptable salt thereof, in an amount from 50 mg per day to 500 mg per day, and tenofovir alafenamide, or a pharmaceutically acceptable salt thereof, in an amount from 60 mg per day to 600 mg per day.

In another embodiment, the present disclosure provides methods of treating HBV infection in a patient in need thereof, comprising administering to the patient Compound B, or a pharmaceutically acceptable salt thereof, in an amount from 50 mg per day to 500 mg per day, and entecavir, or a pharmaceutically acceptable salt, in an amount from 0.1 mg per day to 1 mg per day.

In another embodiment, the present disclosure provides methods of treating HBV infection in a patient in need thereof, comprising administering to the patient Compound B, or a pharmaceutically acceptable salt thereof, in an amount from 75 mg per day to 250 mg per day, and tenofovir, or a pharmaceutically acceptable salt or prodrug thereof, in an amount of 300 mg per day. In an embodiment, the co-administration of Compound B, or a pharmaceutically acceptable salt thereof, and tenofovir, or a pharmaceutically acceptable salt or prodrug thereof, produces a synergistic effect.

In another embodiment, the present disclosure provides methods of treating HBV infection in a patient in need thereof, comprising administering to the patient Compound B, or a pharmaceutically acceptable salt thereof, in an amount from 75 mg per day to 250 mg per day, and tenofovir alafenamide, or a pharmaceutically acceptable salt thereof, in an amount of 300 mg per day. In an embodiment, the co-administration of Compound B, or a pharmaceutically acceptable salt thereof, and tenofovir alafenamide, or a pharmaceutically acceptable salt thereof, produces a synergistic effect.

In another embodiment, the present disclosure provides methods of treating HBV infection in a patient in need thereof, comprising administering to the patient Compound B, or a pharmaceutically acceptable salt thereof, in an amount from 75 mg per day to 250 mg per day, and entecavir, or a pharmaceutically acceptable salt, in an amount of 0.5 mg per day. In an embodiment, the co-administration of Compound B, or a pharmaceutically acceptable salt thereof, and entecavir, or a pharmaceutically acceptable salt, produces a synergistic effect.

In another embodiment, the present disclosure provides methods of treating HBV infection in a patient in need thereof, comprising administering to the patient Compound 8, or a pharmaceutically acceptable salt thereof, in an amount of 250 mg per day, and tenofovir, or a pharmaceutically acceptable salt, or prodrug thereof, in an amount of 300 mg per day.

In another embodiment, the present disclosure provides methods of treating HBV infection in a patient in need thereof, comprising administering to the patient Compound B, or a pharmaceutically acceptable salt thereof, in an amount of 250 mg per day, and tenofovir alafenamide, or a pharmaceutically acceptable salt, in an amount of 300 mg per day.

In another embodiment, the present disclosure provides methods of treating HBV infection in a patient in need thereof, comprising administering to the patient Compound B, or a pharmaceutically acceptable salt thereof, in an amount of 250 mg per day, and entecavir, or a pharmaceutically acceptable salt, in an amount of 0.5 mg per day.

Patients who can be treated using the described methods are in some embodiments human. Other warm-blooded animals can also be treated.

In embodiments of the methods of treating HBV infection provided herein, the patient in need thereof is a chronically HBV-infected patient, with or without evidence of underlying liver inflammation. In some embodiments, the patient has a chronic HBV infection. In other embodiments, the patient is suffering from an HBV-induced disease.

In some embodiments, the HBV-induced disease is cirrhosis, liver failure or hepatocellular carcinoma. In other embodiments, the patient is a treatment-naïve patient. More in particular, the patient is a chronically HBV-infected treatment-naïve patient. In a further embodiment, the patient is HBeAg-positive. In still a further embodiment, the patient is treatment-naïve and HBeAg-positive.

HBV infections that can be treated according to the disclosed methods include HBV genotype A, B, C, and/or D infections. However, in an embodiment, the methods disclosed can treat any HBV genotype ("pan-genotypic treatment"), HBV genotyping can be performed using methods known in the art, for example, INNO-LIPA® HBV Genotyping, Innogenetics N.V., Ghent, Belgium).

The methods of treating HBV infection as provided herein, in particular, treat HBV infection by reducing serum HBV DNA in a patient, by reducing serum HBV RNA in a patient, and/or by reducing serum HBeAg in a patient.

Thus, in an additional embodiment, provided herein is a method of reducing serum HBV DNA in a patient comprising administering to the patient in need thereof a Compound of Formula 1, or a pharmaceutically acceptable salt thereof, in an amount from 50 mg to 500 mg per day.

In another embodiment, provided herein is a method of reducing serum HBV DNA in a patient comprising administering to the patient in need thereof a Compound of Formula 1, or a pharmaceutically acceptable salt thereof, in an amount from 75 mg to 250 mg per day.

In another embodiment, provided herein is a method of reducing serum HBV DNA in a patient comprising administering to the patient in need thereof a Compound of Formula 1, or a pharmaceutically acceptable salt thereof, in an amount of 250 mg per day.

In an additional embodiment, provided herein is a method of reducing serum HBV DNA in a patient comprising administering to the patient in need thereof a Compound of Formula 1, or a pharmaceutically acceptable salt thereof, in an amount from 50 mg to 500 mg per day and tenofovir, or a pharmaceutically acceptable salt or prodrug thereof, in an amount from 60 mg to 600 mg per day.

In another embodiment, provided herein is a method of reducing serum HBV DNA in a patient comprising administering to the patient in need thereof a Compound of Formula 1, or a pharmaceutically acceptable salt thereof, in an amount from 75 mg to 250 mg per day and tenofovir, or a pharmaceutically acceptable salt or prodrug thereof, in an amount of 300 mg per day.

In another embodiment, provided herein is a method of reducing serum HBV DNA in a patient comprising administering to the patient in need thereof a Compound of Formula 1, or a pharmaceutically acceptable salt thereof, in an amount of 250 mg per day and tenofovir, or a pharmaceutically acceptable salt or prodrug thereof, in an amount of 300 mg per day.

In an additional embodiment, provided herein is a method of reducing serum HBV DNA in a patient comprising administering to the patient in need thereof a Compound of Formula 1, or a pharmaceutically acceptable salt thereof, in an amount from 50 mg to 500 mg per day and tenofovir alafenamide, or a pharmaceutically acceptable salt thereof, in an amount from 60 mg to 600 mg per day.

In another embodiment, provided herein is a method of reducing serum HBV DNA in a patient comprising administering to the patient in need thereof a Compound of Formula 1, or a pharmaceutically acceptable salt thereof, in an amount from 75 mg to 250 mg per day and tenofovir alafenamide, or a pharmaceutically acceptable salt thereof, in an amount of 300 mg per day.

In another embodiment, provided herein is a method of reducing serum HBV DNA in a patient comprising administering to the patient in need thereof a Compound of Formula 1, or a pharmaceutically acceptable salt thereof, in an amount of 250 mg per day and tenofovir alafenamide, or a pharmaceutically acceptable salt thereof, in an amount of 300 mg per day.

In an additional embodiment, provided herein is a method of reducing serum HBV DNA in a patient comprising administering to the patient in need thereof a Compound of Formula 1, or a pharmaceutically acceptable salt thereof, in an amount from 50 mg to 500 mg per day and entecavir, or a pharmaceutically acceptable salt thereof, in an amount from 0.1 mg to 1 mg per day.

In another embodiment, provided herein is a method of reducing serum HBV DNA in a patient comprising administering to the patient in need thereof a Compound of Formula 1, or a pharmaceutically acceptable salt thereof, in an amount from 75 mg to 250 mg per day and entecavir, or a pharmaceutically acceptable salt thereof, in an amount of 0.5 mg per day.

In another embodiment, provided herein is a method of reducing serum HBV DNA in a patient comprising administering to the patient in need thereof a Compound of Formula 1, or a pharmaceutically acceptable salt thereof, in an amount of 250 mg per day and entecavir, or a pharmaceutically acceptable salt thereof, in an amount of 0.5 mg per day.

In some embodiments of the method of reducing serum HBV DNA provided herein, the Compound of Formula 1 is Compound A. In some embodiments of the method of reducing serum HBV DNA provided herein, the Compound of Formula 1 is Compound B.

In a further embodiment, the disclosure relates to a method of reducing serum HBV RNA in a patient comprising administering to the patient in need thereof a Compound of Formula 1, or a pharmaceutically acceptable salt thereof, in an amount from 50 mg to 500 mg per day.

In another embodiment, provided herein is a method of reducing serum HBV RNA in a patient comprising administering to the patient in need thereof a Compound of Formula 1, or a pharmaceutically acceptable salt thereof, in an amount from 75 mg to 250 mg per day.

In another embodiment, provided herein is a method of reducing serum HBV RNA in a patient comprising administering to the patient in need thereof a Compound of Formula 1, or a pharmaceutically acceptable salt thereof, in an amount of 250 mg per day.

In an additional embodiment, provided herein is a method of reducing serum HBV RNA in a patient comprising administering to the patient in need thereof a Compound of Formula 1, or a pharmaceutically acceptable salt thereof, in an amount from 50 mg to 500 mg per day and tenofovir, or a pharmaceutically acceptable salt, or prodrug thereof, in an amount from 60 mg to 600 mg per day.

In another embodiment, provided herein is a method of reducing serum HBV RNA in a patient comprising administering to the patient in need thereof a Compound of Formula 1, or a pharmaceutically acceptable salt thereof, in an amount from 75 mg to 250 mg per day and tenofovir, or a pharmaceutically acceptable salt, or prodrug thereof, in an amount of 300 mg per day.

In another embodiment, provided herein is a method of reducing serum HBV RNA in a patient comprising administering to the patient in need thereof a Compound of Formula 1, or a pharmaceutically acceptable salt thereof, in an amount of 250 mg per day and tenofovir, or a pharmaceutically acceptable salt or prodrug thereof, in an amount of 300 mg per day.

In an additional embodiment, provided herein is a method of reducing serum HBV RNA in a patient comprising administering to the patient in need thereof a Compound of Formula 1, or a pharmaceutically acceptable salt thereof, in an amount from 50 mg to 500 mg per day and tenofovir alafenamide, or a pharmaceutically acceptable salt, in an amount from 60 mg to 600 mg per day.

In another embodiment, provided herein is a method of reducing serum HBV RNA in a patient comprising administering to the patient in need thereof a Compound of Formula 1, or a pharmaceutically acceptable salt thereof, in an amount from 75 mg to 250 mg per day and tenofovir alfenamide, or a pharmaceutically acceptable salt, in an amount of 300 mg per day.

In another embodiment, provided herein is a method of reducing serum HBV RNA in a patient comprising administering to the patient in need thereof a Compound of Formula 1, or a pharmaceutically acceptable salt thereof, in an amount of 250 mg per day and tenofovir alefanimide, or a pharmaceutically acceptable salt in an amount of 300 mg per day.

In an additional embodiment, provided herein is a method of reducing serum HBV RNA in a patient comprising administering to the patient in need thereof a Compound of Formula 1, or a pharmaceutically acceptable salt thereof, in an amount from 50 mg to 500 mg per day and entecavir, or a pharmaceutically acceptable salt thereof, in an amount from 0.1 mg to 1 mg per day.

In another embodiment, provided herein is a method of reducing serum HBV RNA in a patient comprising administering to the patient in need thereof a Compound of Formula 1, or a pharmaceutically acceptable salt thereof, in an amount from 75 mg to 250 mg per day and entecavir, or a pharmaceutically acceptable salt thereof, in an amount of 0.5 mg per day.

In another embodiment, provided herein is a method of reducing serum HBV RNA in a patient comprising administering to the patient in need thereof a Compound of Formula 1, or a pharmaceutically acceptable salt thereof, in an amount of 250 mg per day and entecavir, or a pharmaceutically acceptable salt thereof, in an amount of 0.5 mg per day.

In some embodiments of the method of reducing serum HBV RNA provided herein, the Compound of Formula 1 is Compound A. In some embodiments of the method of reducing serum HBV RNA provided herein, the Compound of Formula 1 is Compound B.

In an additional embodiment, the disclosure relates to a method of reducing serum HBeAg in a patient comprising administering to the patient in need thereof a Compound of Formula 1, or a pharmaceutically acceptable salt thereof, in an amount from 50 mg to 500 mg per day.

In another embodiment, provided herein is a method of reducing serum HBeAg in a patient comprising administering to the patient in need thereof a Compound of Formula 1, or a pharmaceutically acceptable salt thereof, in an amount from 75 mg to 250 mg per day.

In another embodiment, provided herein is a method of reducing serum HBeAg in a patient comprising administering to the patient in need thereof a Compound of Formula 1, or a pharmaceutically acceptable salt thereof, in an amount of 250 mg per day.

In an additional embodiment, provided herein is a method of reducing serum HBeAg in a patient comprising administering to the patient in need thereof a Compound of Formula 1, or a pharmaceutically acceptable salt thereof, in an amount from 50 mg to 500 mg per day and tenofovir, or a pharmaceutically acceptable salt, or prodrug thereof, in an amount from 60 mg to 600 mg per day.

In another embodiment, provided herein is a method of reducing serum HBeAg in a patient comprising administering to the patient in need thereof a Compound of Formula 1, or a pharmaceutically acceptable salt thereof, in an amount from 75 mg to 250 mg per day and tenofovir, or a pharmaceutically acceptable salt, or prodrug thereof, in an amount of 300 mg per day.

In another embodiment, provided herein is a method of reducing serum HBeAg in a patient comprising administering to the patient in need thereof a Compound of Formula 1, or a pharmaceutically acceptable salt thereof, in an amount of 250 mg per day and tenofovir, or a pharmaceutically acceptable salt, or prodrug thereof, in an amount of 300 mg per day.

In an additional embodiment, provided herein is a method of reducing serum HBeAg in a patient comprising administering to the patient in need thereof a Compound of Formula 1, or a pharmaceutically acceptable salt thereof, in an amount from 50 mg to 500 mg per day and tenofovir alafenamide, or a pharmaceutically acceptable salt thereof, in an amount from 60 mg to 600 mg per day.

In another embodiment, provided herein is a method of reducing serum HBeAg in a patient comprising administering to the patient in need thereof a Compound of Formula 1, or a pharmaceutically acceptable salt thereof, in an amount from 75 mg to 250 mg per day and tenofovir alafenamide, or a pharmaceutically acceptable salt thereof, in an amount of 300 mg per day.

In another embodiment, provided herein is a method of reducing serum HBeAg in a patient comprising administering to the patient in need thereof a Compound of Formula 1, or a pharmaceutically acceptable salt thereof, in an amount of 250 mg per day and tenofovir aladenamide, or a pharmaceutically acceptable salt thereof, in an amount of 300 mg per day.

In an additional embodiment, provided herein is a method of reducing serum HBeAg in a patient comprising administering to the patient in need thereof a Compound of Formula 1, or a pharmaceutically acceptable salt thereof, in an amount from 50 mg to 500 mg per day and entecavir, or a pharmaceutically acceptable salt thereof, in an amount from 0.1 mg to 1 mg per day.

In another embodiment, provided herein is a method of reducing serum HBeAg in a patient comprising administering to the patient in need thereof a Compound of Formula 1, or a pharmaceutically acceptable salt thereof, in an amount from 75 mg to 250 mg per day and entecavir, or a pharmaceutically acceptable salt thereof, in an amount of 0.5 mg per day.

In another embodiment, provided herein is a method of reducing serum HBeAg in a patient comprising administering to the patient in need thereof a Compound of Formula 1, or a pharmaceutically acceptable salt thereof, in an amount of 250 mg per day and entecavir, or a pharmaceutically acceptable salt thereof, in an amount of 0.5 mg per day.

In some embodiments of the method of reducing serum HBeAg provided herein, the Compound of Formula 1 is Compound A. In some embodiments of the method of reducing serum HBeAg provided herein, the Compound of Formula 1 is Compound B.

Serum HBV DNA quantitation can be performed according to methods known in the art, for example, using the polymerase chain reaction (PCR)-based assay COBAS® TAQMAN® HBV Test v2.0 (Roche Diagnostics), which has been validated to quantify HBV DNA from serum samples for diverse HBV genotypes (A-H) including pre-core mutant HBV strains, with a reported lower limit of detection of 35 IU/mL and a linear dynamic range of quantitation of $1.7 \times 10^2$ to $8.5 \times 10^8$ IU/mL IU/mL, using the WHO pooled serum reference standard for quantitation.

Serum HBsAg and HBeAg levels can be measured using for example, the investigational Abbott ARCHITECT™ assays (Abbott Laboratories; Abbott Park, Ill., USA).

In another aspect, provided herein is a method of decreasing formation of HBV cccDNA in a subject infected with HBV or at risk of being infected with HBV, said method comprising administering to said subject a Compound of Formula 1 at a daily dose of 50-500 mg.

In another embodiment, provided herein is a method of decreasing formation of HBV cccDNA in a subject infected with HBV or at risk of being infected with HBV, said method comprising administering to said subject a Compound of Formula 1 at a daily dose of 75-250 mg.

In another embodiment, provided herein is a method of decreasing formation of HBV cccDNA in a subject infected with HBV or at risk of being infected with HBV, said method comprising administering to said subject a Compound of Formula 1 at a daily dose of 250 mg.

In another embodiment, provided herein is a method of decreasing formation of HBV cccDNA in a subject infected with HBV or at risk of being infected with HBV, said method comprising administering to said subject a Compound of Formula 1 at a daily dose of 50-500 mg; and tenofovir, or a pharmaceutically acceptable salt, or prodrug thereof, at a daily dose of 60-600 mg.

In another embodiment, provided herein is a method of decreasing formation of HBV cccDNA in a subject infected with HBV or at risk of being infected with HBV, said method comprising administering to said subject a Compound of Formula 1 at a daily dose of 75-250 mg; and tenofovir, or a pharmaceutically acceptable salt, or prodrug thereof, at a daily dose of 300 mg.

In another embodiment, provided herein is a method of decreasing formation of HBV cccDNA in a subject infected with HBV or at risk of being infected with HBV, said method comprising administering to said subject a Compound of Formula 1 at a daily dose of 250 mg; and tenofovir, or a pharmaceutically acceptable salt, or prodrug thereof, at a daily dose of 300 mg.

In another embodiment, provided herein is a method of decreasing formation of HBV cccDNA in a subject infected with HBV or at risk of being infected with HBV, said method comprising administering to said subject a Compound of Formula 1 at a daily dose of 50-500 mg; and tenofovir alafenamide, or a pharmaceutically acceptable salt thereof, at a daily dose of 60-600 mg.

In another embodiment, provided herein is a method of decreasing formation of HBV cccDNA in a subject infected with HBV or at risk of being infected with HBV, said method comprising administering to said subject a Compound of Formula 1 at a daily dose of 75-250 mg; and tenofovir alafenamide, or a pharmaceutically acceptable salt thereof, at a daily dose of 300 mg.

In another embodiment, provided herein is a method of decreasing formation of HBV cccDNA in a subject infected with HBV or at risk of being infected with HBV, said method comprising administering to said subject a Compound of Formula 1 at a daily dose of 250 mg; and tenofovir alafenamide, or a pharmaceutically acceptable salt thereof, at a daily dose of 300 mg.

In another embodiment, provided herein is a method of decreasing formation of HBV cccDNA in a subject infected with HBV or at risk of being infected with HBV, said method comprising administering to said subject a Compound of Formula 1 at a daily dose of 50-500 mg; and entecavir, or a pharmaceutically acceptable salt thereof, at a daily dose of 0.1-1 mg.

In another embodiment, provided herein is a method of decreasing formation of HBV cccDNA in a subject infected with HBV or at risk of being infected with HBV, said method comprising administering to said subject a Compound of Formula 1 at a daily dose of 75-250 mg; and entecavir, or a pharmaceutically acceptable salt thereof, at a daily dose of 0.5 mg.

In another embodiment, provided herein is a method of decreasing formation of HBV cccDNA in a subject infected with HBV or at risk of being infected with HBV, said method comprising administering to said subject a Compound of Formula 1 at a daily dose of 250 mg; and entecavir, or a pharmaceutically acceptable salt thereof, at a daily dose of 0.5 mg.

In an embodiment of the method of decreasing formation of HBV cccDNA, a Compound of Formula 1 is formulated with stabilizer. In an embodiment of method of decreasing formation of HBV cccDNA, the stabilizer is HPMC (for example HPMC E5) or HPMC-AS. In an embodiment of the method of decreasing formation of HBV cccDNA, the stabilizer is HPMC (for example HPMC E5). In an embodiment of the method of decreasing formation of HBV cccDNA, the stabilizer is HPMC-AS.

In some embodiments of the method of decreasing formation of HBV cccDNA provided herein, the Compound of Formula 1 is Compound A. In some embodiments of the method of decreasing formation of HBV cccDNA provided herein, the Compound of Formula 1 is Compound B.

In another aspect, provided herein is a method of decreasing HBsAg in a subject infected with HBV or at risk of being infected with HBV, said method comprising administering to said subject a Compound of Formula 1 at a daily dose of 50-500 mg.

In an embodiment, provided herein is a method of decreasing HBsAg in a subject infected with HBV or at risk of being infected with HBV, said method comprising administering to said subject a Compound of Formula 1 at a daily dose of 75-250 mg.

In another embodiment, provided herein is a method of decreasing HBsAg in a subject infected with HBV or at risk of being infected with HBV, said method comprising administering to said subject a Compound of Formula 1 at a daily dose 250 mg.

In another embodiment, provided herein is a method of decreasing HBsAg in a subject infected with HBV or at risk of being infected with HBV, said method comprising administering to said subject a Compound of Formula 1 at a daily dose of 50-500 mg; and tenofovir, or a pharmaceutically acceptable salt, or prodrug thereof, at a daily dose of 60-600 mg.

In an embodiment, provided herein is a method of decreasing HBsAg in a subject infected with HBV or at risk of being infected with HBV, said method comprising administering to said subject a Compound of Formula 1 at a daily dose of 75-250 mg; and tenofovir, or a pharmaceutically acceptable salt, or prodrug thereof, at a daily dose of 300 mg.

In another embodiment, provided herein is a method of decreasing HBsAg in a subject infected with HBV or at risk of being infected with HBV, said method comprising administering to said subject a Compound of Formula 1 at a daily dose 250 mg; and tenofovir, or a pharmaceutically acceptable salt, or prodrug thereof, at a daily dose of 300 mg.

In another embodiment, provided herein is a method of decreasing HBsAg in a subject infected with HBV or at risk of being infected with HBV, said method comprising administering to said subject a Compound of Formula 1 at a daily dose of 50-500 mg; and tenofovir alafenamide, or a pharmaceutically acceptable salt thereof, at a daily dose of 60-600 mg.

In an embodiment, provided herein is a method of decreasing HBsAg in a subject infected with HBV or at risk of being infected with HBV, said method comprising administering to said subject a Compound of Formula 1 at a daily dose of 75-250 mg; and tenofovir alafenamide, or a pharmaceutically acceptable salt thereof, at a daily dose of 300 mg.

In another embodiment, provided herein is a method of decreasing HBsAg in a subject infected with HBV or at risk of being infected with HBV, said method comprising administering to said subject a Compound of Formula 1 at a daily dose 250 mg; and tenofovir alafenamide, or a pharmaceutically acceptable salt thereof, at a daily dose of 300 mg.

In another embodiment, provided herein is a method of decreasing HBsAg in a subject infected with HBV or at risk of being infected with HBV, said method comprising administering to said subject a Compound of Formula 1 at a daily dose of 50-500 mg; and entecavir, or a pharmaceutically acceptable salt thereof, at a daily dose of 0.1-1 mg.

In an embodiment, provided herein is a method of decreasing HBsAg in a subject infected with HBV or at risk of being infected with HBV, said method comprising administering to said subject a Compound of Formula 1 at a daily dose of 75-250 mg; and entecavir, or a pharmaceutically acceptable salt thereof, at a daily dose of 0.5 mg.

In another embodiment, provided herein is a method of decreasing HBsAg in a subject infected with HBV or at risk of being infected with HBV, said method comprising administering to said subject a Compound of Formula 1 at a daily dose 250 mg; and entecavir, or a pharmaceutically acceptable salt thereof, at a daily dose of 0.5 mg.

In some embodiments of the method of decreasing HBsAg, a Compound of Formula 1 is administered in a tablet formulation. In an embodiment of the method of decreasing HBsAg, a Compound of Formula 1 is formulated with stabilizer. In an embodiment of method of decreasing HBsAg, the stabilizer is HPMC (for example HPMC E5) or HPMC-AS. In an embodiment of the method of decreasing HBsAg, the stabilizer is HPMC (for example HPMC E5). In an embodiment of the method of decreasing HBsAg, the stabilizer is HPMC-AS.

In some embodiments of the method of decreasing HBsAg provided herein, the Compound of Formula 1 is Compound A. In some embodiments of the method of decreasing HBsAg provided herein, the Compound of Formula 1 is Compound B.

In yet another aspect, provided herein is a method of preventing HBV infection in a subject at risk of being infected with HBV by decreasing formation of HBV cccDNA, said method comprising administering to said subject a Compound of Formula 1 at a daily dose of 50-500 mg (more particularly at the above-mentioned doses or daily doses).

In an embodiment, provided herein is a method of preventing HBV infection in a subject at risk of being infected with HBV by decreasing formation of HBV cccDNA, said method comprising administering to said subject a Compound of Formula 1 at a daily dose of 75-250 mg (more particularly at the above-mentioned doses or daily doses).

In another embodiment, provided herein is a method of preventing HBV infection in a subject at risk of being infected with HBV by decreasing formation of HBV cccDNA, said method comprising administering to said subject a Compound of Formula 1 at a daily dose of 250 mg.

In an embodiment, provided herein is a method of preventing HBV infection in a subject at risk of being infected with HBV by decreasing formation of HBV cccDNA, said method comprising administering to said subject a Compound of Formula 1 at a daily dose of 50-500 mg (more particularly at the above-mentioned doses or daily doses); and tenofovir, or a pharmaceutically acceptable salt, or prodrug thereof, at a daily dose of 60-600 mg.

In an embodiment, provided herein is a method of preventing HBV infection in a subject at risk of being infected with HBV by decreasing formation of HBV cccDNA, said method comprising administering to said subject a Compound of Formula 1 at a daily dose of 75-250 mg (more particularly at the above-mentioned doses or daily doses); and tenofovir, or a pharmaceutically acceptable salt, or prodrug thereof, at a daily dose of 300 mg.

In another embodiment, provided herein is a method of preventing HBV infection in a subject at risk of being infected with HBV by decreasing formation of HBV cccDNA, said method comprising administering to said subject a Compound of Formula 1 at a daily dose of 250 mg; and tenofovir, or a pharmaceutically acceptable salt, or prodrug thereof, at a daily dose of 300 mg.

In an embodiment, provided herein is a method of preventing HBV infection in a subject at risk of being infected with HBV by decreasing formation of HBV cccDNA, said method comprising administering to said subject a Compound of Formula 1 at a daily dose of 50-500 mg (more particularly at the above-mentioned doses or daily doses); and tenofovir alafenamide, or a pharmaceutically acceptable salt thereof, at a daily dose of 60-600 mg.

In an embodiment, provided herein is a method of preventing HBV infection in a subject at risk of being infected with HBV by decreasing formation of HBV cccDNA, said method comprising administering to said subject a Compound of Formula 1 at a daily dose of 75-250 mg (more particularly at the above-mentioned doses or daily doses); and tenofovir alafenamide, or a pharmaceutically acceptable salt thereof, at a daily dose of 300 mg.

In another embodiment, provided herein is a method of preventing HBV infection in a subject at risk of being infected with HBV by decreasing formation of HBV cccDNA, said method comprising administering to said subject a Compound of Formula 1 at a daily dose of 250 mg; and tenofovir alafenamide, or a pharmaceutically acceptable salt, at a daily dose of 300 mg.

In an embodiment, provided herein is a method of preventing HBV infection in a subject at risk of being infected with HBV by decreasing formation of HBV cccDNA, said method comprising administering to said subject a Compound of Formula 1 at a daily dose of 50-500 mg (more particularly at the above-mentioned doses or daily doses); and entecavir, or a pharmaceutically acceptable salt thereof, at a daily dose of 0.1-1 mg.

In an embodiment, provided herein is a method of preventing HBV infection in a subject at risk of being infected with HBV by decreasing formation of HBV cccDNA, said method comprising administering to said subject a Compound of Formula 1 at a daily dose of 75-250 mg (more particularly at the above-mentioned doses or daily doses); and entecavir, or a pharmaceutically acceptable salt thereof, at a daily dose of 0.5 mg.

In another embodiment, provided herein is a method of preventing HBV infection in a subject at risk of being infected with HBV by decreasing formation of HBV cccDNA, said method comprising administering to said subject a Compound of Formula 1 at a daily dose of 250 mg; and entecavir, or a pharmaceutically acceptable salt thereof, at a daily dose of 0.5 mg.

In some embodiments of the method of preventing HBV infection by decreasing formation of HBV cccDNA, a Compound of Formula 1 is administered in a tablet formulation. In an embodiment of the method of preventing HBV infection by decreasing formation of HBV cccDNA, a Compound of Formula 1 is formulated with stabilizer. In an embodiment of the method of preventing HBV infection by decreasing formation of HBV cccDNA, the stabilizer is HPMC (for example HPMC E5) or HPMC-AS. In an embodiment of the method of preventing HBV infection by decreasing formation of HBV cccDNA, the stabilizer is HPMC (for example HPMC E5). In an embodiment of the method of preventing HBV infection by decreasing formation of HBV cccDNA, the stabilizer is HPMC-AS.

In some embodiments of the method of preventing HBV infection by decreasing formation of HBV cccDNA provided herein, the Compound of Formula 1 is Compound A. In some embodiments of the method of preventing HBV infection by decreasing formation of HBV cccDNA provided herein, the Compound of Formula 1 is Compound B.

In an aspect of the methods provided herein, the particular dosing strategy results in inhibition of DANE particles, RNA-containing particles, and double-stranded DNA particles but does not inhibit subviral particles containing HBsAg.

In another aspect of the methods provided herein, the particular dosing strategy results in the inhibition of cccDNA, which results in inhibition of subviral particles containing HBsAg.

In some embodiments, a Compound of Formula 1 is administered in a tablet formulation. In an embodiment, a Compound of Formula 1 is formulated with stabilizer. In an embodiment, the stabilizer is HPMC (for example HPMC E5) or HPMC-AS. In an embodiment, the stabilizer is HPMC (for example HPMC E5). In an embodiment, the stabilizer is HPMC AS.

In an embodiment, the tablet comprises a Compound of Formula 1 and stabilizer at a ratio of 1:1, 1:2, 1:3, 1:4, or 1:5.

In a particular embodiment, the tablet comprises a Compound of Formula 1 and stabilizer at a ratio of 1:3.

In another embodiment, the tablet comprises 50-500 mg of a Compound of Formula 1 (more particularly at the above-mentioned doses or daily doses) and 150-1500 mg of stabilizer, more particularly 50-1500 mg of stabilizer. In another embodiment, the tablet comprises 75-250 mg of a Compound of Formula 1 (more particularly at the above-mentioned doses or daily doses) and 225-750 mg of stabilizer, more particularly 75-750 mg of stabilizer. In another embodiment, the tablet comprises 250 mg of a Compound of Formula 1 and 750 mg of stabilizer.

A tablet of the application may further comprise one or several agents selected from fillers, disintegrants, glidants and lubricants. For example, a tablet of the application may further comprise at least one filler selected from microcrystalline cellulose, silicified microcrystalline cellulose and pre-gelatinized maize starch, at least one disintegrant such as croscarmellose sodium, at least one glidant such as colloidal anhydrous silica, and at least one lubricant such as magnesium stearate.

In some embodiments, the administration of a Compound of Formula 1 is performed for an administration period of about 24 weeks. In another embodiment, the administration of a Compound of Formula 1 is performed for an administration period of longer than 24 weeks. In yet another embodiment, the administration of a Compound of Formula 1 is performed for an administration period shorter than 24 weeks (e.g., 10, 12, 14, 16, 18, 20, or 22 weeks). In embodiments, a Compound of Formula 1 is administered for a duration of 28 days. In embodiments, a Compound of Formula 1 is administered for a duration of about 48 weeks. In embodiments, a Compound of Formula 1 is administered for a duration of longer than 48 weeks.

In some embodiments, the co-administration of a Compound of Formula 1 and the transcription inhibitor is performed for an administration period of about 24 weeks. In another embodiment, the administration of a Compound of Formula 1 and the transcription inhibitor is performed for an administration period of longer than 24 weeks. In yet another embodiment, the administration of a Compound of Formula 1 and the transcription inhibitor is performed for an administration period shorter than 24 weeks (e.g., 10, 12, 14, 16, 18, 20, or 22 weeks). In embodiments, a Compound of Formula 1 and the transcription inhibitor is administered for a duration of 28 days. In embodiments, a Compound of Formula 1 and the transcription inhibitor is administered for a duration of about 48 weeks. In embodiments, a Compound of Formula 1 and the transcription inhibitor is administered for a duration of longer than 48 weeks.

In some embodiments, the co-administration of a Compound of Formula 1 and the nucleos(t)ide analogue is performed for an administration period of about 24 weeks. In another embodiment, the administration of a Compound of Formula 1 and the nucleos(t)ide analogue is performed for an administration period of longer than 24 weeks. In yet another embodiment, the administration of a Compound of Formula 1 and the nucleos(t)ide analogue is performed for an administration period shorter than 24 weeks (e.g., 10, 12, 14, 16, 18, 20, or 22 weeks). In embodiments, a Compound of Formula 1 and the nucleos(t)ide analogue is administered for a duration of 28 days. In embodiments, a Compound of Formula 1 and the nucleos(t)ide analogue is administered for a duration of about 48 weeks. In embodiments, a Compound of Formula 1 and the nucleos(t)ide analogue is administered for a duration of longer than 48 weeks.

In some embodiments, the co-administration of a Compound of Formula 1 and tenofovir is performed for an administration period of about 24 weeks. In another embodiment, the administration of a Compound of Formula 1 and tenofovir is performed for an administration period of longer than 24 weeks. In yet another embodiment, the administration of a Compound of Formula 1 and tenofovir is performed for an administration period shorter than 24 weeks (e.g., 10, 12, 14, 16, 18, 20, or 22 weeks). In embodiments, a Compound of Formula 1 and tenofovir is administered for a duration of 28 days. In embodiments, a Compound of Formula 1 and tenofovir is administered for a duration of about 48 weeks. In embodiments, a Compound of Formula 1 and tenofovir is administered for a duration of longer than 48 weeks.

In some embodiments, the co-administration of a Compound of Formula 1 and tenofovir alafenamide is performed for an administration period of about 24 weeks. In another embodiment, the administration of a Compound of Formula 1 and tenofovir alafenamide is performed for an administration period of longer than 24 weeks. In yet another embodiment, the administration of a Compound of Formula 1 and tenofovir alafenamide is performed for an administration period shorter than 24 weeks (e.g., 10, 12, 14, 16, 18, 20, or 22 weeks). In embodiments, a Compound of Formula 1 and tenofovir alafenamide is administered for a duration of 28 days. In embodiments, a Compound of Formula 1 and tenofovir alafenamide is administered for a duration of about 48 weeks. In embodiments, a Compound of Formula 1 and tenofovir alafenamide is administered for a duration of longer than 48 weeks.

In some embodiments, the co-administration of a Compound of Formula 1 and entecavir is performed for an administration period of about 24 weeks. In another embodiment, the administration of a Compound of Formula 1 and entecavir is performed for an administration period of longer than 24 weeks. In yet another embodiment, the administration of a Compound of Formula 1 and entecavir is performed for an administration period shorter than 24 weeks (e.g., 10, 12, 14, 16, 18, 20, or 22 weeks). In embodiments, a Compound of Formula 1 and entecavir is administered for a duration of 28 days. In embodiments, a Compound of Formula 1 and entecavir is administered for a duration of about 48 weeks. In embodiments, a Compound of Formula 1 and entecavir is administered for a duration of longer than 48 weeks.

In some embodiments, the administration of Compound A is performed for an administration period of about 24 weeks. In another embodiment, the administration of Compound A is performed for an administration period of longer than 24 weeks. In yet another embodiment, the administration of Compound A is performed for an administration period shorter than 24 weeks (e.g., 10, 12, 14, 16, 18, 20, or 22 weeks). In embodiments, Compound A is administered for a duration of 28 days. In embodiments, Compound A is administered for a duration of about 48 weeks. In embodiments, Compound A is administered for a duration of longer than 48 weeks.

In some embodiments, the co-administration of Compound A and the transcription inhibitor is performed for an administration period of about 24 weeks. In another embodiment, the administration of Compound A and the transcription inhibitor is performed for an administration period of longer than 24 weeks. In yet another embodiment, the administration of Compound A and the transcription inhibitor is performed for an administration period shorter than 24 weeks (e.g., 10, 12, 14, 16, 18, 20, or 22 weeks). In embodiments, Compound A and the transcription inhibitor is administered for a duration of 28 days. In embodiments, Compound A and the transcription inhibitor is administered for a duration of about 48 weeks. In embodiments, Compound A and the transcription inhibitor is administered for a duration of longer than 48 weeks.

In some embodiments, the co-administration of Compound A and the nucleos(t)ide analogue is performed for an administration period of about 24 weeks. In another embodiment, the administration of Compound A and the nucleos(t)ide analogue is performed for an administration period of longer than 24 weeks. In yet another embodiment, the administration of Compound A and the nucleos(t)ide analogue is performed for an administration period shorter than 24 weeks (e.g., 10, 12, 14, 16, 18, 20, or 22 weeks). In embodiments, Compound A and the nucleos(t)ide analogue is administered for a duration of 28 days. In embodiments, Compound A and the nucleos(t)ide analogue is administered for a duration of about 48 weeks. In embodiments, Compound A and the nucleos(t)ide analogue is administered for a duration of longer than 48 weeks.

In some embodiments, the co-administration of Compound A and tenofovir is performed for an administration period of about 24 weeks. In another embodiment, the administration of Compound A and tenofovir is performed for an administration period of longer than 24 weeks. In yet another embodiment, the administration of Compound A and tenofovir is performed for an administration period shorter than 24 weeks (e.g., 10, 12, 14, 16, 18, 20, or 22 weeks). In embodiments, Compound A and tenofovir is administered for a duration of 28 days. In embodiments, Compound A and tenofovir is administered for a duration of about 48 weeks. In embodiments, Compound A and tenofovir is administered for a duration of longer than 48 weeks.

In some embodiments, the co-administration of Compound A and tenofovir alafenamide is performed for an administration period of about 24 weeks. In another embodiment, the administration of Compound A and tenofovir alafenamide is performed for an administration period of longer than 24 weeks. In yet another embodiment, the administration of Compound A and tenofovir alafenamide is performed for an administration period shorter than 24 weeks (e.g., 10, 12, 14, 16, 18, 20, or 22 weeks). In embodiments, Compound A and tenofovir alafenamide is administered for a duration of 28 days. In embodiments, Compound A and tenofovir alafenamide is administered for a duration of about 48 weeks. In embodiments, Compound A and tenofovir alafenamide is administered for a duration of longer than 48 weeks.

In some embodiments, the co-administration of Compound A and entecavir is performed for an administration period of about 24 weeks. In another embodiment, the administration of Compound A and entecavir is performed for an administration period of longer than 24 weeks. In yet another embodiment, the administration of Compound A and entecavir is performed for an administration period shorter than 24 weeks (e.g., 10, 12, 14, 16, 18, 20, or 22 weeks). In embodiments, Compound A and entecavir is administered for a duration of 28 days. In embodiments, Compound A and entecavir is administered for a duration of about 48 weeks. In embodiments, Compound A and entecavir is administered for a duration of longer than 48 weeks.

In some embodiments, the administration of Compound B is performed for an administration period of about 24 weeks. In another embodiment, the administration of Compound B is performed for an administration period of longer than 24 weeks. In yet another embodiment, the administration of Compound B is performed for an administration period shorter than 24 weeks (e.g., 10, 12, 14, 16, 18, 20, or 22 weeks). In embodiments, Compound B is administered for a duration of 28 days. In embodiments, Compound B is administered for a duration of about 48 weeks. In embodiments, Compound B is administered for a duration of longer than 48 weeks.

In some embodiments, the co-administration of Compound B and the transcription inhibitor is performed for an administration period of about 24 weeks. In another embodiment, the administration of Compound B and the transcription inhibitor is performed for an administration period of longer than 24 weeks. In yet another embodiment, the administration of Compound B and the transcription inhibitor is performed for an administration period shorter than 24 weeks (e.g., 10, 12, 14, 16, 18, 20, or 22 weeks). In embodiments, Compound B and the transcription inhibitor is administered for a duration of 28 days. In embodiments, Compound B and the transcription inhibitor is administered for a duration of about 48 weeks. In embodiments, Compound B and the transcription inhibitor is administered for a duration of longer than 48 weeks.

In some embodiments, the co-administration of Compound B and the nucleos(t)ide analogue is performed for an administration period of about 24 weeks. In another embodiment, the administration of Compound B and the nucleos(t)ide analogue is performed for an administration period of longer than 24 weeks. In yet another embodiment, the administration of Compound B and the nucleos(t)ide analogue is performed for an administration period shorter than 24 weeks (e.g., 10, 12, 14, 16, 18, 20, or 22 weeks). In embodiments, Compound B and the nucleos(t)ide analogue is administered for a duration of 28 days. In embodiments, Compound B and the nucleos(t)ide analogue is administered for a duration of about 48 weeks. In embodiments, Compound B and the nucleos(t)ide analogue is administered for a duration of longer than 48 weeks.

In some embodiments, the co-administration of Compound B and tenofovir is performed for an administration period of about 24 weeks. In another embodiment, the administration of Compound B and tenofovir is performed for an administration period of longer than 24 weeks. In yet another embodiment, the administration of Compound B and tenofovir is performed for an administration period shorter than 24 weeks (e.g., 10, 12, 14, 16, 18, 20, or 22 weeks). In embodiments, Compound B and tenofovir is administered for a duration of 28 days. In embodiments, Compound B and tenofovir is administered for a duration of about 48 weeks. In embodiments, Compound B and tenofovir is administered for a duration of longer than 48 weeks.

In some embodiments, the co-administration of Compound B and tenofovir alafenamide is performed for an administration period of about 24 weeks. In another embodiment, the administration of Compound B and tenofovir alafenamide is performed for an administration period of longer than 24 weeks. In yet another embodiment, the administration of Compound B and tenofovir alafenamide is performed for an administration period shorter than 24 weeks (e.g., 10, 12, 14, 16, 18, 20, or 22 weeks). In embodiments, Compound B and tenofovir is administered for a duration of 28 days. In embodiments, Compound B and tenofovir alafenamide is administered for a duration of about 48 weeks. In embodiments, Compound B and tenofovir is administered for a duration of longer than 48 weeks.

In some embodiments, the co-administration of Compound B and entecavir is performed for an administration period of about 24 weeks. In another embodiment, the administration of Compound B and entecavir is performed for an administration period of longer than 24 weeks. In yet another embodiment, the administration of Compound B and entecavir is performed for an administration period shorter than 24 weeks (e.g., 10, 12, 14, 16, 18, 20, or 22 weeks). In embodiments, Compound B and entecavir is administered for a duration of 28 days. In embodiments, Compound B and entecavir is administered for a duration of about 48 weeks. In embodiments, Compound B and entecavir is administered for a duration of longer than 48 weeks.

In some embodiments of the methods provided herein, a Compound of Formula 1 is in the form of a spray dried power. In other embodiments of the methods provided herein, the spray dried powder is formulated in a tablet, or in a capsule, or in a suspension in water, or in a suspension in an aqueous buffer solution. In other embodiments of the methods provided herein, each of these formulations are for oral administration to the subject. In particular embodiments of the methods provided herein, a Compound of Formula 1 is administered orally as a 5 mg, 25 mg, or 100 mg tablet.

In embodiments of the methods provided herein, the Compound of Formula 1 is administered to reach a maximal concentration (Cmax) of at least 3,000 ng/mL (e.g., at steady state), in the plasma of the patient and/or an AUC of at least 50,000 ng·h/mL (e.g., at steady state), in the plasma of the patient.

In embodiments of the methods provided herein, Compound A is administered to reach a maximal concentration (Cmax) of at least 3,000 ng/mL, in the plasma of the patient and/or an AUC of at least 50,000 ng·h/mL, in the plasma of the patient.

In embodiments of the methods provided herein, Compound B is administered to reach a maximal concentration (Cmax) of at least 3,000 ng/mL, in the plasma of the patient and/or an AUC of at least 50,000 ng·h/mL, in the plasma of the patient.

The daily doses described herein are calculated for an average body weight of about 60 to about 70 kg and should be recalculated in case of paediatric applications, or when used with patients with a substantially diverting body weight.

Pharmaceutical Compositions and Kits

In an aspect, provided herein is a pharmaceutical composition comprising a Compound of Formula 1, or a pharmaceutically acceptable salt thereof, in an amount of 50-500 mg.

In another aspect, the present disclosure provides a pharmaceutical product comprising a pharmaceutical composition comprising a Compound of Formula 1, or a pharmaceutically acceptable salt thereof, and a pharmaceutically acceptable carrier or diluent. In some embodiments, the pharmaceutical composition comprises a Compound of Formula 1, or a pharmaceutically acceptable salt thereof, in an amount that is from about 50 mg to about 500 mg (more particularly at the above-mentioned doses or daily doses), and a pharmaceutically acceptable carrier or diluent. In certain embodiments, the pharmaceutical composition comprises an amount of a Compound of Formula 1 selected from 50, 75, 100, 150, 250, 300, 400, and 500 mg. In another embodiment, the pharmaceutical composition comprises an amount of a Compound of Formula 1 is 250 mg.

In an embodiment of the pharmaceutical composition, the composition further comprises at least one stabilizer. In some embodiments of the pharmaceutical composition, the one or more stabilizers are selected from HPMC (for example HPMC E5) and HPMC-AS. In an embodiment, at least one of the stabilizers is HPMC (for example HPMC E5). In an embodiment, at least one of the stabilizers is HPMC-AS.

In an embodiment of the pharmaceutical composition, the composition comprises a Compound of Formula 1 and stabilizer at a ratio of 1:1, 1:2, 1:3, 1:4, or 1:5. In a particular embodiment, the composition comprises a Compound of Formula 1 and stabilizer at a ratio of 1:3.

In another embodiment of the pharmaceutical composition, the composition comprises 50-500 mg of a Compound of Formula 1 and 150-1500 mg of stabilizer, more particularly 50-1500 mg of stabilizer. In another embodiment of the pharmaceutical composition, the composition comprises 75-250 mg of a Compound of Formula 1 (more particularly at the above-mentioned doses or daily doses) and 225-750 mg of stabilizer, more particularly 75-750 mg of stabilizer. In another embodiment of the pharmaceutical composition, the composition comprises 250 mg of a Compound of Formula 1 and 750 mg of stabilizer.

The pharmaceutical composition can be formulated as a solid formulation, such as a tablet, a pill or a capsule, or as a liquid formulation such as a polyethylene glycol solution.

The pharmaceutical composition can be formulated for oral administration.

In another aspect, the present disclosure provides a kit of parts for treating HBV infections, comprising a Compound of Formula 1, or a pharmaceutically acceptable salt thereof, in an amount from 50 mg per day to 500 mg (more particularly at the above-mentioned doses or daily doses), and a transcription inhibitor. In another embodiment, the present disclosure provides a kit of parts for treating HBV infections, comprising a Compound of Formula 1, or a pharmaceutically acceptable salt thereof, in an amount from 50 mg to 500 mg (more particularly at the above-mentioned doses or daily doses) and a nucleos(t)ide analogue. In another embodiment, the present disclosure provides a kit of parts for treating HBV infections, comprising a Compound of Formula 1, or a pharmaceutically acceptable salt thereof, in an amount from 50 mg to 500 mg (more particularly at the above-mentioned doses or daily doses) and tenofovir, or a pharmaceutically acceptable salt, or prodrug thereof, in an amount of 60 mg to 600 mg. In another embodiment, the present disclosure provides a kit of parts for treating HBV infections, comprising a Compound of Formula 1, or a pharmaceutically acceptable salt thereof, in an amount from 50 mg to 500 mg (more particularly at the above-mentioned daily doses) and entecavir, or a pharmaceutically acceptable salt, in an amount of 0.1 mg to 1 mg. In some embodiments, the kit of parts further comprises packaging and instructions.

In some embodiments, the kit of parts comprises a pharmaceutical composition comprising a Compound of Formula 1, or a pharmaceutically acceptable salt thereof; an additional HBV antiviral agent; and a pharmaceutically acceptable carrier or diluent.

The additional HBV antiviral agent can e.g., be an immune modulator (such as interferon), at least one Nucleic Acid Polymer (more particularly at least one NAP which inhibits the release of subviral particles from hepatocytes), or at least one small interfering RNA (siRNA) or antisense oligonucleotide (more particularly at least one siRNA or ASO selected from the group of siRNAs and ASOs which inhibit the expression of one or more genes that are necessary for replication or pathogenesis of HBV).

In another embodiment, the kit of parts comprises a pharmaceutical product comprising:

a pharmaceutical composition comprising a Compound of Formula 1:

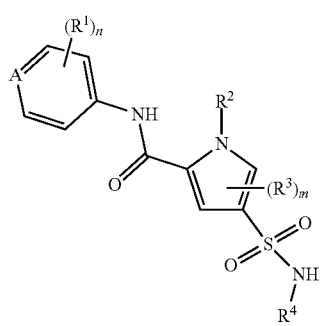
(1)

or a pharmaceutically acceptable salt thereof, wherein:

A is N or CH;

$R^1$ is, independently at each occurrence, selected from halo, $CF_3$, and CN;

$R^2$ is $C_1$-$C_3$ alkyl;

$R^3$ is, independently at each occurrence, selected from $C_1$-$C_3$ alkyl and halo;

$R^4$ is $C_1$-$C_4$ alkyl, which is independently substituted 1 or 2 times with halo or $CF_3$;

n is 0, 1, 2, or 3; and m is 0, 1, or 2;

in an amount from 50 mg to 500 mg (more particularly at the above-mentioned doses or daily doses), and a pharmaceutically acceptable carrier or diluent; and a nucleos(t)ide analogue;

a sealed container for housing the pharmaceutical composition;

a sealed contained for housing the nucleos(t)ide analogue; and instructions for use.

In additional embodiments, pharmaceutical kits are provided. The kit includes a sealed container approved for the storage of pharmaceutical compositions, the container containing one of the above-described pharmaceutical compositions. In some embodiments, the sealed container minimizes the contact of air with the ingredients, e.g. an airless bottle. In other embodiments, the sealed container is a sealed tube. An instruction for the use of the composition and the information about the composition are to be included in the kit.

In some embodiments of the kit of parts provided herein, the Compound of Formula 1 is Compound A:

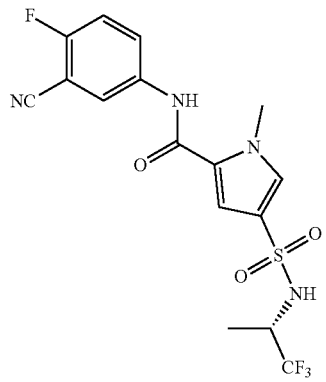
(A)

or a pharmaceutically acceptable salt thereof.

In other embodiments of the kit of parts provided herein, the Compound of Formula 1 is Compound B:

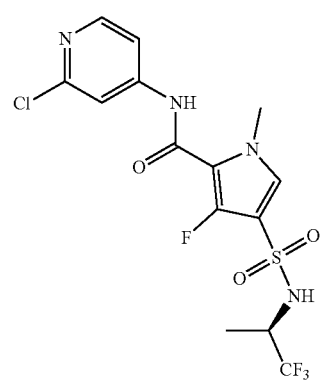
(B)

or a pharmaceutically acceptable salt thereof.

The following examples are merely illustrative and are not intended to limit the disclosure to the materials, conditions, or process parameters set forth therein.

EXAMPLES

Example 1: Safety, Pharmacokinetics and Antiviral Activity of Compound A in Treatment Naïve Patients with Chronic HBV In part 1 of this study (FIG. 1, sessions 1-7), it was shown that Compound A was well tolerated in healthy subjects at single doses of up to 600 mg, and at multiple doses of 150 mg for two days followed by 100 mg once a day for 10 days.

In part 2 of this study (FIG. 1, sessions 8-9), the objective was to evaluate the safety, PK, and antiviral activity of Compound A in treatment naïve, chronic hepatitis B patients over a 28-day treatment period. The patient criteria were:

HBeAg-positive or negative

Plasma HBV DNA>2.0 log 10 IU/mL

ALT/AST<2.5×ULN

METAVIR stage<F3.

1.1 Patient Baseline Characteristics

The baseline characteristics of the patients in the study are described in Table 1 below.

TABLE 1

Baseline Patient Characteristics

| Analysis set: Intent-to-treat | Session 8 (n = 12)* | Session 9 (n = 12)* |
|---|---|---|
| Mean age, years (SD) | 39.5 (11.6) | 36.5 (10.2) |
| Sex-Male, n (%) | 11 (92) | 10 (83) |
| Race-White, n (%) | 6 (50) | 12 (100) |
| HBeAg positive, n (%) | 6 (50) | 3 (25) |
| Mean HBV DNA $\log_{10}$ IU/mL (SD) | 6.41 (1.99) | 5.36 (1.54) |
| ALT Grade, n (%) | | |
| Grade 0 | 9 (75) | 9 (75) |
| Grade 1 | 3 (25) | 3 (25) |
| Fibrosis stage n, (%) | | |
| F0 | 4 (33) | 5 (42) |
| F1 | 6 (50) | 4 (33) |
| F2 | 2 (17) | 3 (25) |
| HBV genotype, n (%) | n = 10 | n = 9 |
| A | 2 (20) | 1 (11) |
| C | 2 (20) | 0 |
| D | 5 (50) | 8 (89) |
| E | 1 (10) | 0 |

The study showed that there were no serious adverse events (SAES) or adverse events (AEs) of clinical concern and no treatment discontinuations. Further, no patients showed clinically significant ECG changes or persistent/worsening vital sign abnormalities (see Table 2 below). Although no patients had Grade 3 or 4 AEs on treatment, one patient had Grade 1 & 2 ALT and Grade 1 AST elevations on treatment that rose to Grade 3 & 4 ALT and Grade 3 AST elevations in follow up. No treatment-emergent Grade 3 or 4 laboratory abnormalities were reported, with the exception of the Grade 3 amylase increase.

TABLE 2

Evaluation of Adverse Events

| | 25 mg Compound A (100 mg Day 1; n = 8) | 75 mg Compound A (n = 8) | Pooled placebo (n = 8) |
|---|---|---|---|
| On-treatment AEs (28 days) | | | |
| At least one AE | 5 (63) | 4 (50) | 5 (63) |
| Worst Grade 1 AEs, n (%) | 3 (38) | 2 (25) | 4 (50) |
| Worst Grade 2 AEs, n (%) | 1 (13) | 1 (13) | 1 (13) |
| Worst Grade 3 AEs, n (%) | 1 (13) | 0 (0)* | 0 (0) |
| Most common AEs (≥2 patients) | | | |
| Amylase Increased | 2 (25)** | 0 | 0 |
| Headache | 2 (25) | 0 | 3 (38) |

1.2 Pharmacokinetics

Figure 2:
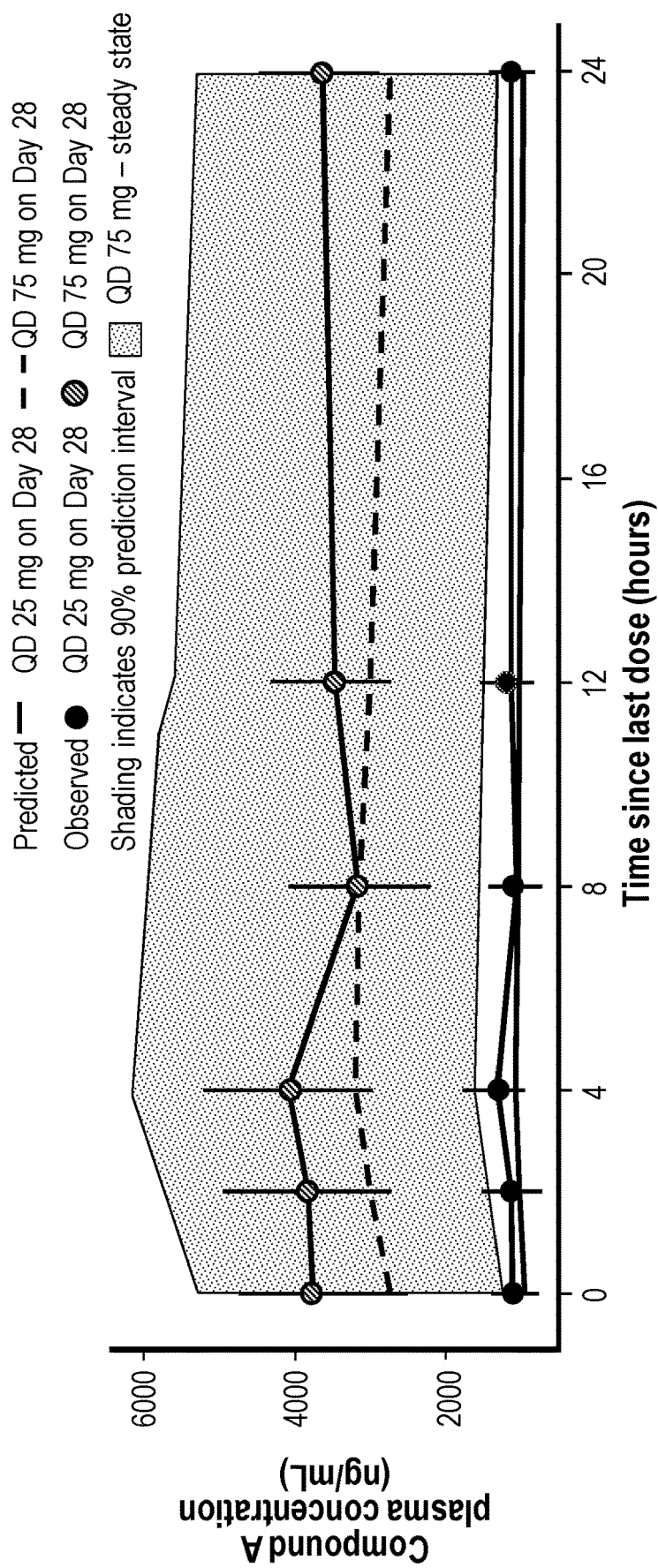
FIG. 2 depicts the plasma concentration of Compound A in human subjects following 28 day treatment.

FIG. 2 shows that the pharmacokinetics were dose-proportional and apparent clearance was low in both treatment arms. The exposure (Cmax, AUC) increased in a dose-dependent manner with time-linear PK. The pharmacokinetics of Compound A were not markedly different between healthy volunteers and patients. Mean Compound A exposures in patients with CHB could be predicted from data in healthy volunteers. Mean (±SD) exposure in the 75 mg arm was within 90% prediction interval. Mean dose normalized Cmax at steady state was 56.6 ng/mL (25 mg) and 53.2 ng/mL (75 mg). Mean dose normalized AUC 0-24 h was 1109 ng·h/mL for both the 25 mg and 75 mg groups. Apparent clearance was low and similar in the two dosing groups (1 and 0.9 L/h at 25 mg and 75 mg, respectively).

1.3 HBV Reduction

Figure 3:
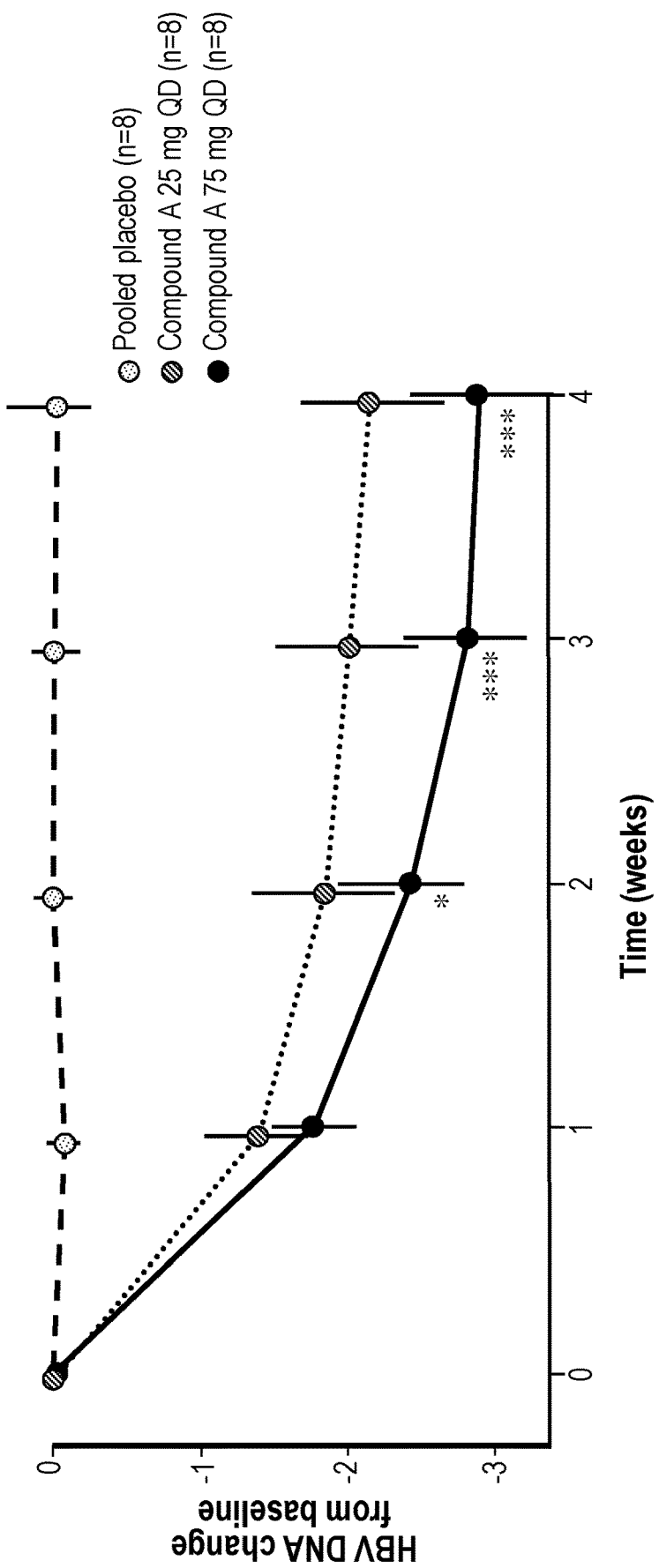
FIG. 3 depicts the effect of Compound A on HBV DNA. * and *** refer respectively to one and three patients with HBV DNA less than the lower limit of quantitation in the HBV DNA assay. Placebo data is pooled from both sessions. Values are mean±SD

HBV DNA was assessed for each patient weekly during this study (see FIG. 3). A mean reduction in plasma HBV DNA levels of 2.16 (±0.49 SD) $\log_{10}$ IU/mL (25 mg Compound A) and 2.89 (±0.48 SD) $\log_{10}$ IU/mL (75 mg Compound A) from baseline was observed after 28 days. Three patients dosed with 75 mg QD achieved HBV DNA below the level of quantification of the HBV DNA assay while none in the 25 mg Compound A group achieved this. A more pronounced and consistent decline in HBV DNA was observed across patients in the 75 mg group compared with the 25 mg group. Consistent with HBV DNA, substantial reductions in HBV RNA levels were observed with Compound A treatment, although baseline levels were low (see Table 3 below).

TABLE 3

HBV DNA and RNA analysis

| | | HBV DNA | | | | HBV RNA | | |
|---|---|---|---|---|---|---|---|---|
| | | Baseline | Day 29 Mean (SD) Change | | | Baseline* | Day 29 Mean (SD) Change | |
| Treatment arm | N | Mean (SD) $\log_{10}$ IU/mL | from Baseline $\log_{10}$ IU/mL | <LLOQ | N | Mean (SD) $\log_{10}$ cp/mL | from Baseline $\log_{10}$ cp/mL | Not detected |
| 25 mg QD | 8 | 6.90 (1.91) | −2.16 (0.49) | 0 | 8 | 5.60 (2.37) | −2.30 (0.59) | 3 |
| 75 mg QD | 8 | 5.26 (1.50) | −2.89 (0.48) | 3 | 8 | 3.39 (2.21) | −1.85 (1.42) | 6 |
| Pooled placebo | 8 | 5.49 (1.77) | −0.01 (0.31) | 0 | 8 | 4.03 (2.64) | −0.18 (0.72) | 2 |

1.4 Conclusions

Across the two dose groups (n=24), patients had a median age of 36 years (range: 21-58) with 88% males and 75% Caucasian. Overall, 38% of patients were HBeAg-positive, and mean (±SD) baseline HBV DNA was 5.88 (±1.82) log 10 IU/mL. AEs or laboratory abnormalities Grade 3 were infrequent (≤2 patients/dose). Of patients treated with Compound A, 56% (9/16) experienced at least one adverse event (AE) during treatment (5 patients in the 25 mg arm, and 4 patients in the 75 mg arm) compared to 63% (5/8) in the placebo arm. There were no serious AEs, no discontinuations due to AEs, and no dose-limiting toxicities. After 28 days, mean (±SD) reductions in HBV DNA levels from baseline of 2.16 (±0.49) log 10 IU/mL (25 mg QD) and 2.89 (±0.48) log 10 IU/mL (75 mg QD) were observed. Three patients dosed with 75 mg QD achieved HBV DNA below the level of quantification of the HBV DNA assay but no patients dosed with 25 mg QD reached HBV DNA below quantification. In addition, a decline in HBV RNA levels was observed in both Compound A treatment groups; while reduction in HBV RNA was higher in the 25 mg group than the 75 mg group, more patients in the 75 mg (n=6) than the 25 mg group (n=3) achieved HBV RNA below the level of quantification of the HBV RNA assay.

Figure 4:
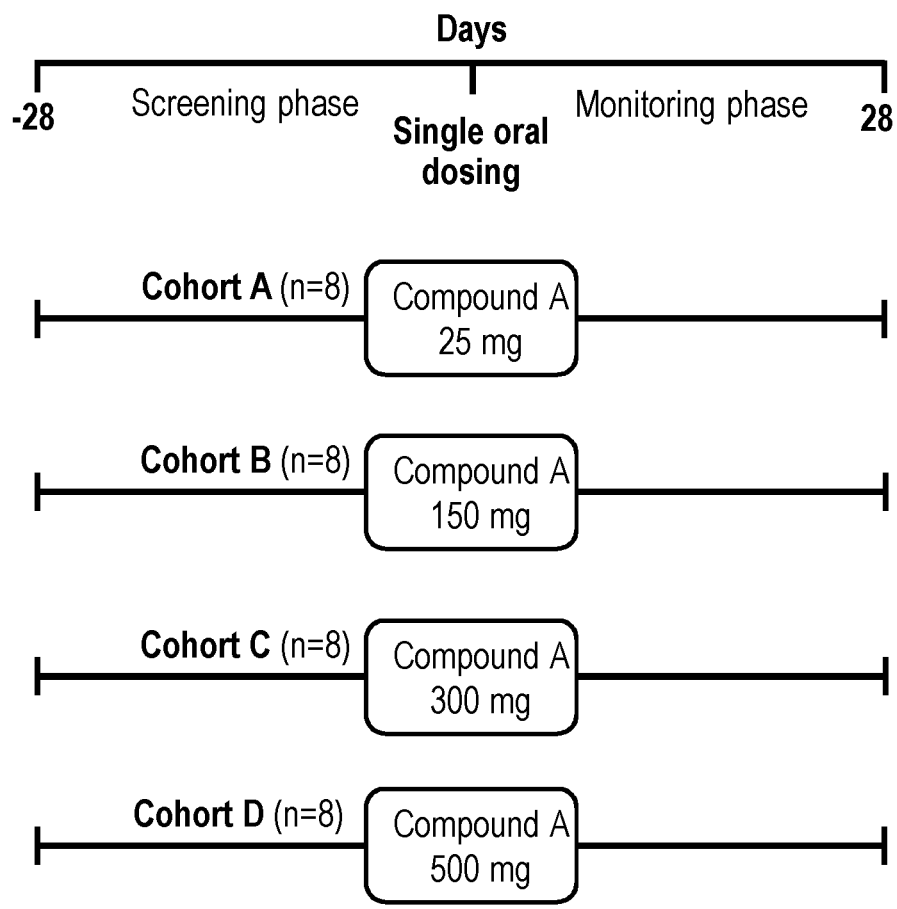
FIG. 4 depicts the study design for testing the safety and tolerability of Compound A in healthy human subjects.

Example 2: Safety, Tolerability and Pharmacokinetics of Single Ascending Doses of Compound A in Healthy Subjects A double-blind, placebo-controlled study was done to assess the safety, tolerability, and pharmacokinetics (PK) of Compound A. Thirty-two healthy adult Japanese volunteers were randomized into four cohorts. The volunteers were randomized 3:1 to receive a single dose of Compound A or placebo in a fasted state (see FIG. 4). The safety, tolerability and PK plasma profiles of Compound A were assessed after each dose. Full plasma PK profiles were determined up to 28 days after each single dose of Compound A. Urinary elimination was assessed in Cohort C (see FIG. 4) for 7 day.

2.1 Healthy Volunteers Baseline Characteristics

The baseline characteristics of the subjects are summarized in Table 4 below.

TABLE 4

Baseline Patient Characteristics

| | | Compound A | | | |
|---|---|---|---|---|---|
| | Placebo (n = 8) | 25 mg (n = 6) | 150 mg (n = 6) | 300 mg (n = 6) | 500 mg (n = 6) |
| Median age (years [range]) | 47.0 (32; 54) | 34.0 (32; 51) | 31.5 (26; 55) | 40.0 (31; 55) | 42.0 (28; 55) |
| Sex, n (%) Male | 7 (88) | 6 (100) | 6 (100) | 5 (83) | 4 (67) |
| Race Asian | 8 (100) | 6 (100) | 6 (100) | 6 (100) | 6 (100) |
| Median BMI (kg/m$^2$) | 22.90 | 23.29 | 21.74 | 24.40 | 22.25 |

Compound A was well tolerated. No volunteers experienced an SAE or prematurely discontinued the study for an AE. The treatment emergent adverse events (TEAEs) reported reported were hiccups, upper respiratory tract infection, nasal congestion, and cough. All TEAEs were mild and were resolved before the end of the study. The AEs are summarized in Table 6 below.

TABLE 5

Adverse Events

| | Compound A | | | | | |
|---|---|---|---|---|---|---|
| | Placebo (n = 8) | 25 mg (n = 6) | 150 mg (n = 6) | 300 mg (n = 6) | 500 mg (n = 6) | Total (n = 32) |
| | Treatment-emergent AEs | | | | | |
| Volunteers with ≥0.1 AE | 0 | 0 | 2 (33) | 0 | 2 (33) | 4 (17) |
| Related to Compound A | 0 | 0 | 0 | 0 | 0 | 0 |
| SAEs | 0 | 0 | 0 | 0 | 0 | 0 |
| Deaths | 0 | 0 | 0 | 0 | 0 | 0 |

No significant laboratory abnormalities were discovered, most laboratory abnormalities were Grade 1. No Grade 3 or 4 abnormalities were reported. The laboratory abnormalities from the study are summarized in Table 6 below.

TABLE 6

Laboratory Abnormalities

| | Compound A | | | | | |
|---|---|---|---|---|---|---|
| | Placebo (n = 8) | 25 mg (n = 6) | 150 mg (n = 6) | 300 mg (n = 6) | 500 mg (n = 6) | Total (n = 32) |
| | Grade 2 AEs | | | | | |
| Bilirubin increased | 0 | 0 | 0 | 0 | 0 | 0 |
| Cholesterol increased | 0 | 0 | 0 | 0 | 0 | 0 |
| Triglycerides increased | 1 (13) | 1 (17) | 0 | 1 (17) | 0 | 2 (8) |
| Leukocytes decreased | 0 | 0 | 0 | 0 | 0 | 0 |
| Fibrinogen decreased | 0 | 0 | 0 | 0 | 0 | 0 |

2.2 Pharmacokinetics

Figure 5:
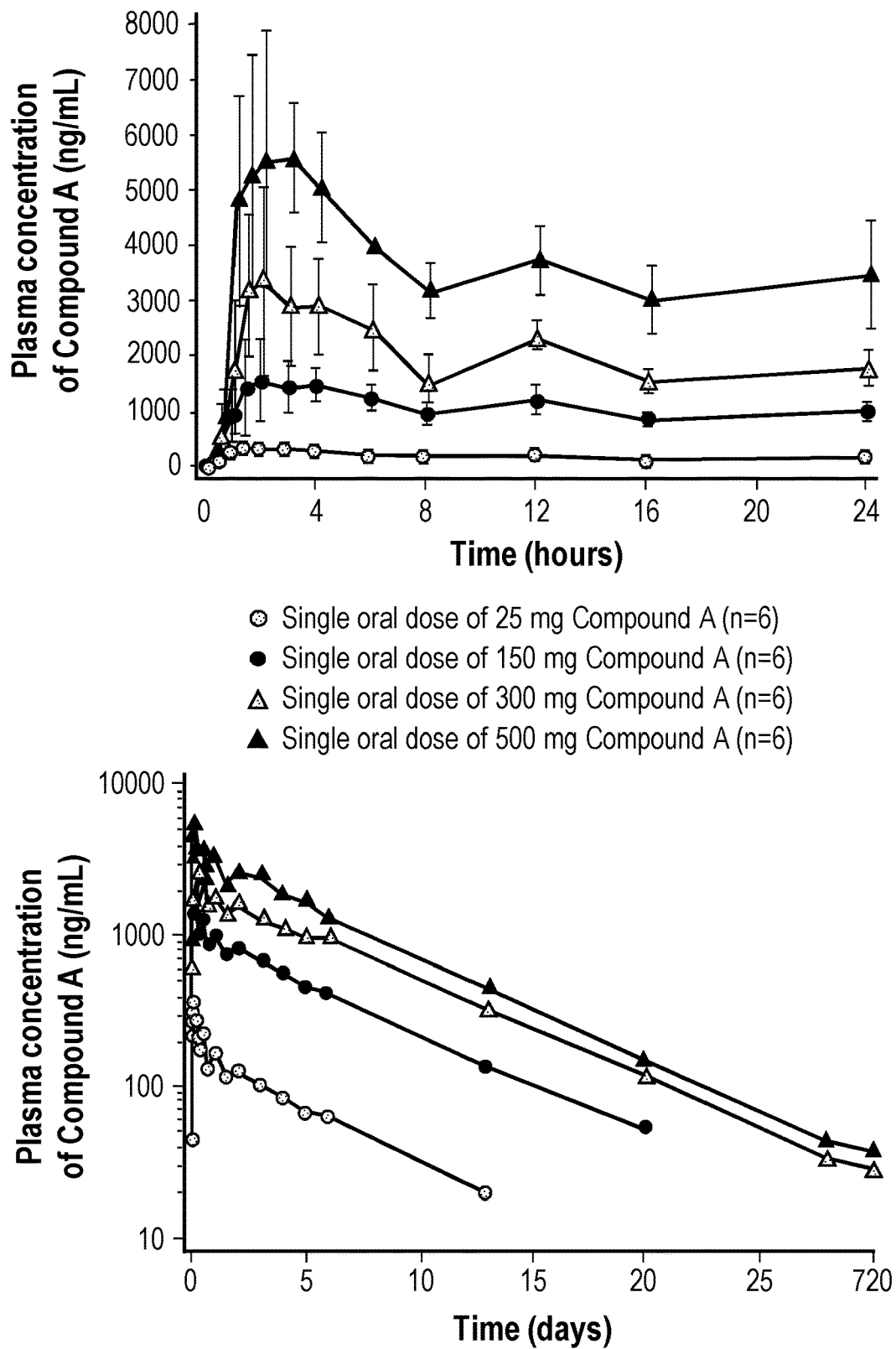
FIG. 5 depicts the pharmacokinetics of Compound A in healthy human subjects.

The PKs were dose-dependent in all four treatment cohorts. The PK data is summarized in FIG. 5 and Table 7 below. Mean values of CUF, Vd/F and T½term were comparable between dose levels. The inter-subject variability, expressed as % CV, was low to moderate and similar across dose levels. After single dose administration of 300 mg of Compound A in Cohort C, 53.9 mg of the unchanged drug was excreted in urine, Compound A is a low clearance drug, with 18% of the administered dose excreted via the kidneys,

TABLE 7

Pharmacokinetics

| | Compound A | | | |
|---|---|---|---|---|
| Pharmacokinetics | 25 mg (n = 6)* | 160 mg (n = 6) | 300 mg (n = 6) | 500 mg (n = 6) |
| Median $t_{max}$, h (range) | 1.75 (1.00-2.00) | 3.00 (1.50-6.00) | 3.00 (1.50-6.00) | 1.75 (1.00-3.00) |
| Mean $C_{max}$, ng/mL (SD)‡ | 375 (89.8) | 296 (88.8) | 308 (131) | 328 (88.1) |
| Dose normalised $AUC_{24\,h}$, ng · h/mL (SD)‡ | 4627 (687) | 4298 (739) | 4012 (885) | 4382 (792) |
| Mean $t_{1/2\,term}$, h (SD) | 106.3 (35.9) | 100.2 (31.1) | 115.9 (27.2) | 95.6 (36.5) |

TABLE 7-continued

Pharmacokinetics

| | Compound A | | | |
|---|---|---|---|---|
| Pharmacokinetics | 25 mg (n = 6)* | 160 mg (n = 6) | 300 mg (n = 6) | 500 mg (n = 6) |
| Mean CL/F, L/h (SD) | 1.03 (0.33) | 0.929 (0.24) | 0.852 (0.17) | 0.919 (0.23) |
| Mean $V_d$/F, L (SD) | 132 (17.8) | 126 (12.9) | 1137 (16.3) | 119 (20.7) |

Example 3: Formulations of Compound A

The quantitative and qualitative composition of the Compound A 250 mg/g spray dried powder (G001) is provided in Table 8 below.

TABLE 8

Quantitative and Qualitative Composition of the Compound A 250 mg/g Spray Dried Powder (G001)

| Component | Quality Reference | Function | Quantity (mg) |
|---|---|---|---|
| Comppund A | Company specification | Active | 250 |
| Hydroxypropyl methylcellulose E5 [b] | Ph. Eur., NF | Stabilizer | 750 |
| Methanol[a] | Ph. Eur., NF | Solvent | — |
| Methylene Chloride[a] | Ph. Eur., NF | Solvent | — |
| Total | | | 1,000 |

[a]Removed during processing
[b]Hydroxypropyl methylcellulose (HPMC) is also called Hypromellose The qualitative and quantitative composition of the Compound A 100-mg (G009) 25-mg (G008) and 5-mg (G007) oral tablets is provided in Table 9 below.

TABLE 9

Qualitative and Quantitative Composition of Compound A 100-mg oral tablets (G009), 25-mG tablets (G008) and 5-mg tablets (G007)

| Component | Quality Reference | Function | Quantity per Tablet (mg) G009 | Quantity per Tablet (mg) G008 | Quantity per Tablet (mg) G007 |
|---|---|---|---|---|---|
| 250 mg/g spray dried powder (G001) | Company specifications | Active | 400.00 | 100.00 | 20.00 |
| Microcrystalline cellulose | Ph. Eur., NF | Filler | 477.70 | 119.42 | 177.66 |
| Mannitol | Ph. Eur., NF | Filler | 178.30 | 44.58 | 66.34 |
| Croscarmellose sodium | Ph. Eur., NF | Disintegrant | 120.00 | 30.00 | 30.00 |
| Colloidal anhydrous silica | Ph. Eur., NF | Glidant | 12.00 | 3.00 | 3.00 |
| Magnesium stearate[a] | Ph. Eur., NF | Lubricant | 12.00 | 3.00 | 3.00 |
| Nominal Weight | | | 1,200.00 | 300.00 | 300.00 |

[a]Sourced from vegetable origin.

The quantitative and qualitative composition of the Compound A 250 mg/g spray dried powder (G021) is provided in Table 10 below.

TABLE 10

Quantitative and Qualitative Composition of the Compound A 250 mg/g Spray Dried Powder (G021)

| Component | Quality Reference | Function | Quantity (mg) |
|---|---|---|---|
| Compound A | Company specification | Active | 250 |
| Hypromellose acetate succinate (HPMC-AS)[a] | NF | Stabilizer | 750 |
| Methanol[b] | Ph. Eur. | Solvent | — |
| Methylene Chloride[b] | Ph. Eur. | Solvent | — |
| Total | | | 1,000 |

[a]Hypromellose acetate succinate (HPMC-AS) is also called hydroxypropyl methylcellulose acetate succinate
[b]Removed during processing The qualitative and quantitative composition of the Compound A 100-mg (G022) oral tablets is provided in Table 11 below.

TABLE 11

Qualitative and Quantitative Composition of Compound A 100-mg oral tablets (G022), 100-mg oral tablets (G024) and 25-mg oral tablets (G025)

| Component | Quality Reference | Function | Quantity per Tablet (mg) G022 | Quantity per Tablet (mg) G024 | Quantity per Tablet (mg) G025 |
|---|---|---|---|---|---|
| Intragranular Phase | | | | | |
| 250 mg/g spray dried powder (G021) | Company specifications | Active | 400.00 | 400.00 | 100.00 |
| Microcrystalline cellulose | Ph. Eur. | Filler | 400.00 | 256.00 | 64.00 |
| Croscarmellose sodium | Ph. Eur. | Disintegrant | 30.00 | 30.00 | 7.50 |
| Colloidal anhydrous silica | Ph. Eur. | Glidant | 6.00 | 6.00 | 1.50 |
| Magnesium stearate, NF[a] | Ph. Eur. | Lubricant | 3.00 | 3.00 | 0.75 |
| Extragranular Phase | | | | | |
| Silicified Microcrystalline Cellulose | NF | Filler | 316.00 | 394.00 | 98.50 |
| Croscarmellose sodium | Ph. Eur. | Disintegrant | 30.00 | 30.00 | 7.50 |
| Colloidal anhydrous silica | Ph. Eur. | Glidant | 6.00 | 6.00 | 1.50 |
| Magnesium stearate, NF[a] | Ph. Eur. | Lubricant | 9.00 | 9.00 | 2.25 |
| Pre-gelatinized Maize Starch | Ph. Eur | Filler | — | 66.00 | 16.50 |
| Nominal Weight | | | 1,200.00 | 1,200.00 | 300.00 |

[a]Vegetable grade

Example 4: Bioavailability of Tablets G009 and G022

A Phase 1, Open-label Study in Healthy Adult Subjects has been conducted to assess the bioavailability of single doses of a compound of formula (1) administered as oral tablets (pharmacokinetic analysis).

Tablets G009 or tablets G022 (cf. Tables 10 and 11 of example 3 above) were administered as 300-mg single oral doses in healthy adult subjects under fasted and fed conditions. A total of 28 subjects was enrolled in the study, equally divided over 2 cohorts (14 subjects per cohort).

In Part I of the study, all subjects in a cohort (n=14) received a single oral 300-mg dose of compound of formula (1), formulated as 3×100-mg test tablets in Treatment Period 1 (tablet G022, Treatment A), followed by a single oral 300 mg dose of compound of formula (1), formulated as 3×100-mg tablets in Treatment Period 2 (tablets G009, Treatment B). Both treatments were administered under fasted conditions on Day 1.

In Part I, study drug intake in Treatment Periods 1 and 2 in an individual subject were separated by a washout period of at least 37 days.

In Part II, all subjects in a cohort (n=14) received a single oral 300-mg dose of compound of formula (1), formulated as 3×100-mg G022 tablets in Treatment Period 1 (Treatment C). Treatment C was administered under fed conditions on Day 1.

Full pharmacokinetic (PK) profiles of compound of formula (A) were determined over approximately 864 hours (37 days) after compound of formula (A) drug administration on Day 1 of all treatments in Parts I and II.

TABLE 12

| | Pharmacokinetics | | |
|---|---|---|---|
| (mean [SD], $t_{max}$: $t_{last}$: median [range]) | 300 mg API tablets G022 single dose, fasted Treatment A | 300 mg API tablets G009 single dose, fasted Treatment B | 300 mg API tablets G022 single dose, fed Treatment C |
| n | 14 | 12[a] | 13[b] |
| $C_{max}$ (ng/mL) | 3105 (631) | 2121 (615) | 2522 (606) |
| $t_{max}$ (h) | 3.00 (0.99-8.00) | 2.99 (1.00-12.01) | 4.00 (1.50-12.00) |
| $C_{last}$ (ng/mL) | 58.3 (65.8) | 54.8 (65.2) | 41.1 (27.9) |
| $t_{last}$ (h) | 815.91 (312.00-840.63) | 816.00 (480.05-840.00) | 480.00 (456.00-864.46) |
| $AUC_{72\,h}$ (ng · h/mL) | 107309 (17414) | 93105 (18074) | 108211 (23333) |
| $AUC_{last}$ (ng · h/mL) | 331296 (123779) | 326043 (119556) | 296699 (87563) |
| $AUC_\infty$ (ng · h/mL) | 345465 (148016) | 343222 (151988) | 302793 (90245) |
| $t_{1/2}$ (h) | 124.6 (57.7) | 142.2 (76.2) | 95.7 (31.3) |
| CL/F (L/h) | 1.00 (0.419) | 0.994 (0.342) | 1.09 (0.367) |
| $V_d/F$ (L) | 156 (24.4) | 177 (32.4) | 141 (34.9) |

[a] n = 13 for $C_{max}$ and $t_{max}$
[b] n = 14 for $C_{max}$, $t_{max}$, and $AUC_{72\,h}$

TABLE 13

| | Effect of Formulation | | | | |
|---|---|---|---|---|---|
| | Geometric Mean | | | | |
| Pharmacokinetic Parameter | Treatment B 300 mg API tablets G009 single dose, fasted | Treatment A 300 mg API tablets G022 single dose, fasted | Geometric Mean Ratio, (%) | 90% CI, (%) | Intra-subject CV, (%) |
| n | 12[a] | 14 | | | |
| $C_{max}$ (ng/mL) | 2047 | 3043 | 148.70 | 127.46-173.48 | 22.8 |
| $AUC_{72\,h}$ (ng · h/mL) | 91062 | 106032 | 116.44 | 108.61-124.83 | 9.6 |
| $AUC_{last}$ (ng · h/mL) | 290089 | 311608 | 107.42 | 100.76-114.52 | 8.8 |
| $AUC_\infty$ (ng · h/mL) | 300237 | 321212 | 106.99 | 100.26-114.16 | 8.9 |

[a] n = 13 for $C_{max}$

TABLE 14

| | Effect of Food | | | | |
|---|---|---|---|---|---|
| | Geometric Mean | | | | |
| Pharmacokinetic Parameter | Treatment A 300 mg API tablets G022 single dose, fasted | Treatment C 300 mg API tablets G022 single dose, fed | Geometric Mean Ratio, (%) | 90% CI, (%) | Inter-subject CV, (%) |
| n | 14 | 13[a] | | | |
| $C_{max}$ (ng/mL) | 3043 | 2440 | 80.18 | 68.25-94.20 | 25.4 |
| $AUC_{72\,h}$ (ng · h/mL) | 106032 | 105647 | 99.64 | 87.54-113.40 | 20.3 |
| $AUC_{last}$ (ng · h/mL) | 311608 | 284160 | 91.19 | 72.81-114.22 | 35.2 |
| $AUC_\infty$ (ng · h/mL) | 321212 | 289763 | 90.21 | 71.30-114.13 | 36.9 |

[a] n = 14 for $C_{max}$ and $AUC_{72\,h}$

TABLE 15

| | |
|---|---|
| $C_{max}$ | Maximum observed analyte concentration; |
| $t_{max}$ | Actual sampling time to reach the maximum observed analyte concentration; |
| $C_{last}$ | Last observed measurable (non-below quantification limit [non-BQL]) plasma analyte concentration; |
| $t_{last}$ | Actual sampling time of last measurable (non-BQL) plasma analyte concentration; |
| $AUC_{72\,h}$ | Area under the analyte concentration-time curve (AUC) from time 0 to 72 hours postdose, calculated by linear-linear trapezoidal summation; |
| $AUC_{last}$ | Area under the analyte concentration vs time curve from time 0 to time of the last measurable (non-BQL) concentration, calculated by linear-linear trapezoidal summation; |
| $AUC_\infty$ | Area under the analyte concentration-time curve from time 0 to infinite time, calculated as $AUC_{last} + C_{last}/\lambda_z$, where $C_{last}$ is the last observed measurable (non-BQL) concentration; extrapolations of more than 20.00% of the total AUC are reported as approximations; |
| $t_{1/2}$ | Apparent terminal elimination half-life, calculated as $0.693/\lambda_z$; |
| $\lambda_z$ | Apparent terminal elimination rate constant, estimated by linear regression using the terminal log-linear phase of the log transformed concentration versus time curve; |
| CL/F | Total apparent oral clearance, calculated as dose/$AUC_\infty$; |
| $Vd_z$/F | Apparent volume of distribution, calculated as dose/$(\lambda_z * AUC_\infty)$. |

Non-compartmental analysis (Model Type: Plasma [200-202], Dose Type: Extravascular) was applied for the PK analysis. Furthermore, SAS (version 9.3, SAS Institute Inc., Cary, N.C., USA) was used, predominantly for the creation of PK tables.

Effect of Formulation (G022 Versus G009)

Based on the geometric mean ratios, of tablets G022 provide a 1.49-fold higher Cmax than tablets G009, both under fasted conditions at a 300 mg-dose. AUC72 h, AUClast, and AUC∞ were similar (90% CIs of the geometric mean ratios within 80-125%) for both tablet formulations.

Median tmax was the same for tablets G022 (3.00 hours) and tablets G009 (2.99 hours) under fasted conditions.

Under fasted conditions, mean t½ was 124.6 hours for tablets G022 and 142.2 hours for tablets G009.

Effect of Food

Based on the geometric mean ratios between intake of tablets G022 under fed conditions and under fasted conditions, Cmax, AUClast, and AUC∞ were modestly lower (by 19.82%, 8.81% and 9.79%, respectively) after intake under fed conditions, while AUC72 h was similar for both treatments (300 mg-dose). The lower limits of the 90% CIs of the geometric mean ratios of Cmax, AUClast, and AUC∞ fell below 80%. There was one subject in Part 1, who showed relatively high $AUC_{last}$ and $AUC_\infty$ values as compared to other subjects, due to slower elimination of compound A. The $AUC_{last}$ and $AUC_\infty$ values for this subject may explain the modestly lower geometric mean values in Treatment C compared to Treatment A.

For tablets G022, median tmax occurred somewhat later under fed conditions compared to administration under fasted conditions, respectively 4.00 hours and 3.00 hours postdose.

Mean t½ was in the same range after intake of tablets G022 under fasted and fed conditions, with values of 124.6 hours (fasted) and 95.7 hours (fed).

Example 5: Bioavailability of Tablets G009 and G024

The protocol of bioavailability study that has been described for tablets G009 and G022 (in example 4 above) can be applied to tablets G009 and G024.

Example 6

The primary objectives were to evaluate the oral bioavailability of Compound A when administered as single dose of 150 mg, composed of 6×25-mg oral tablets, under fasted and fed conditions, and as single dose of 300 mg, composed of 3×100-mg oral tablets, under fasted conditions in healthy adult subjects Part I was conducted to assess the bioavailability of new 25 mg oral tablets of Compound A under fasted and fed conditions, and of new 100 mg oral tablets of Compound A under fasted conditions, in healthy adult subjects. In Treatment Period 1 of Part I, all 16 subjects received a single 150 mg dose (6×25 mg oral tablets) under fed conditions (Treatment A). Thereafter, subjects were randomly assigned to either Arm 1 or Arm 2 in a 1:1 ratio. In Arm 1, subjects received a single 150 mg dose (6×25 mg oral tablets) under fasted conditions in Treatment Period 2 (Treatment B). In Arm 2, subjects received a single 300 mg dose (3×100 mg oral tablets) under fasted conditions in Treatment Period 2 (Treatment C).

Full pharmacokinetic (PK) profiles of Compound A were determined over approximately 768 hours (33 days) after Compound A administration on Day 1 of each treatment period. Safety and tolerability were assessed throughout the study.

In Part I, 16 healthy adult subjects were included. After Treatment A (150 mg Compound A, fed) in Treatment Period 1, subjects were randomly assigned to either Arm 1 (n=8; Treatment B [150 mg Compound A, fasted]) or Arm 2 (Treatment C [n=7; 300 mg Compound A, fasted]) in a 1:1 ratio in Treatment Period 2. Fifteen subjects completed study participation in Part I, but all 16 subjects were included in the PK and safety analyses.

Healthy male and female subjects between 18 and 55 years of age (inclusive), who had a body mass index (BMI) between 18.0 and 30.0 kg/m2 (extremes included), and a body weight of not less than 50.0 kg, were eligible for enrollment into the study. Subjects had to be healthy on the basis of medical and surgical history, physical examination, 12 lead electrocardiogram (ECG), vital signs, and clinical laboratory tests performed at screening. Male and female subjects had to adhere to the contraceptive requirements as specified in the protocol.

TABLE 16

| Treatment | Dose (Formulation) |
|---|---|
| A | 150 mg (6 tablets of 25 mg) |
| B | 150 mg (6 tablets of 25 mg) |
| C | 300 mg (3 tablets of 100 mg) |

The study consisted of a screening phase, an admission phase, a treatment phase, and a follow-up phase (posttreatment phase). During the follow-up phase, subjects returned to the study site 10-14 days and 30-35 days after study drug administration in the last treatment period for a follow-up visit. The duration of each treatment phase was 33±3 days and the study duration per individual subject was at least 61 days (including admission and follow-up period), screening period not included.

Study Population:

A total of 16 subjects were enrolled and received Treatment A in Period 1. One subject prematurely terminated the study (withdrawal of consent by subject) after having received Treatment A in Period 1. Fifteen subjects were randomized to Treatment B (N=8) or Treatment C (N=7) and completed treatment and the study as planned.

TABLE 17

Summary of Demographics and Baseline Characteristics: Part 1; Safety Analysis Set

| Analysis set: Safety, N | 16 |
|---|---|
| Age, years | |
| Median | 47.0 |
| Range | (19; 55) |
| Sex | |
| Male | 13 (81.3%) |
| Female | 3 (18.8%) |
| Race | |
| Asian | 1 (6.3%) |
| Black or African American | 1 (6.3%) |
| White | 14 (17.5%) |
| Body Mass Index, kg/m$^2$ | |
| Median | 25.75 |
| Range | (19.3; 29.7) |

Note:
SD = Standard Deviation
Screening values have been considered as baseline characteristics for all the parameters.

TABLE 18

PHARMACOKINETIC RESULTS:

Pharmacokinetics of Compound A

| (Mean [SD], $t_{max}$: Median [Range]) | 150 mg Compound A 6 × 25 mg Fed (Standard Breakfast) Treatment A | 150 mg Compound A 6 × 25 mg Fasting Treatment B | 300 mg Compound A 3 × 100 mg Fasting Treatment C |
|---|---|---|---|
| n | 16 | 8 | 7 |
| $C_{max}$ (ng/mL) | 1543 (279) | 1918 (458) | 2773 (460) |
| $t_{max}$ (h) | 4.00 (1.00-4.05) | 1.75 (1.00-3.00) | 3.00 (1.00-4.02) |
| $AUC_{last}$ (ng · h/mL) | 171012 (45636) | 176800 (34478) | 371406 (123728) |
| $AUC_{\infty}$ (ng · h/mL) | 177482 (47313) | 181907 (35169) | 392969 (142342) |
| Dose normalized PK parameters[a] | | | |
| $C_{max}$ (ng/mL) | 257 (46.5) | 320 (76.3) | 231 (38.3) |
| $AUC_{last}$ (ng · h/mL) | 28502 (7606) | 29467 (5746) | 30951 (10311) |
| $AUC_{\infty}$ (ng · h/mL) | 29580 (7886) | 30318 (5861) | 32747 (11862) |

[a]dose normalized to 25 mg.

Food Effect

The statistical results comparing the PK of Compound A between Treatment A and Treatment B (food effect) are presented in the table below.

TABLE 19

| Pharmacokinetic Parameters Compound A | Geometric Mean | | Geometric Mean Ratio, (%) | 90% CI, (%) |
|---|---|---|---|---|
| | 150 mg Compound A 6 × 25 mg Fasting Treatment B (Reference) | 150 mg Compound A 6 × 25 mg Fed (Standard Breakfast) Treatment A (Test) | | |
| n | 8 | 16 | | |
| $C_{max}$ (ng/mL) | 1766 | 1516 | 85.84 | 77.01-95.68 |
| $AUC_{last}$ (ng · h/mL) | 163356 | 165071 | 101.05 | 96.86-105.42 |
| $AUC_\infty$ (ng · h/mL) | 168064 | 171275 | 101.91 | 96.66-107.45 |

Based on the geometric mean ratios between Treatment A (fed, test, n=16) and Treatment B (fasted, reference, n=8), Cmax was 14.2% (GMR, 85.8%; 90% Cl, 77.0-95.7%) lower under fed conditions, while AUClast and AUC∞ were similar under fasted or fed conditions. The upper limit of the 90% Cl of the geometric mean ratio of Cmax fell below 100%.

Effect of Tablet Strength

The statistical results comparing the dose normalized PK parameters of Compound A (effect of tablet strength) between Treatments B and C are presented in the table below.

TABLE 20

| Pharmacokinetic Parameters Compound A | Geometric Mean | | Geometric Mean Ratio, (%) | 90% CI, (%) |
|---|---|---|---|---|
| | 150 mg Compound A 6 × 25 mg Fasting Treatment B (Reference) | 300 mg Compound A 3 × 100 mg Fasting Treatment C Test | | |
| n | 8 | 7 | | |
| $C_{max, dose\ normalized}$ (ng/mL)$^a$ | 294 | 231 | 78.44 | 67.44-91.22 |
| $AUC_{last, dose\ normalized}$ (ng · h/mL)$^a$ | 27226 | 30835 | 113.26 | 106.48-120.47 |
| $AUC_{\infty, dose\ normalized}$ (ng · h/mL)$^a$ | 28011 | 32329 | 115.42 | 106.86-124.66 |

$^a$dose normalized to 25 mg.

Based on the geometric mean ratios between Treatment C and Treatment B of the dose normalized PK parameters, Cmax was 21.6% (GMR, 78.4%; 90% Cl, 67.4-91.2%) lower for the 100 mg tablet strength compared to the 25 mg tablet strength. The upper limit of the 90% Cl of the geometric mean ratio of Cmax fell below 100%. The AUClast and AUC∞ were similar under fasted or fed conditions.

Median (range) tmax was 1.75 (1.00-3.00) hours when 150 mg Compound A was dosed as 6×25 mg oral tablets, and 3.00 (1.00-4.02) hours when 300 mg Compound A was dosed as 3×100 mg oral tablets.

Mean (range) t½term was similar between treatments. Values ranged between subjects, namely 134.3 (65.7-221.6) hours, 123.9 (72.3-195.7) hours, and 161.1 (111.5-257.3) hours for Treatment A, B, and C, respectively.

Clearance (CUF) ranged between 0.47 and 1.55 L/h over all treatments and individuals.

Example 7: Therapeutic Exploratory Phase II Study on Compound A in Patients with Chronic HBV Infection A double-blind, placebo-controlled study is done to evaluate efficacy of 24 weeks of Compound A treatment, either alone or in combination with a nucleoside analogue, in terms of changes in hepatitis B surface antigen (HBsAg) levels.

7.1 Patient Baseline Characteristics

Treatment naïve, adult patients with chronic HBV infection are randomized for the study.

7.2 Dosing and Combinations

Compound A is administered at 250 mg per day in a tablet formulation by oral administration. Compound A is administered either alone or in combination with a nucleoside analogue. The nucleoside analogue is either tenofovir disoproxil fumarate (Viread, Gilead Sciences International) administered at 300 mg per day in a film-coated tablet by oral administration or entecavir monohydrate (Baraclude, Bristol-Myers Squibb Pharma) administered at 0.5 mg per day in a film-coated tablet by oral administration.

7.3 Results

This study evaluates the safety and tolerability of 24 weeks of study treatment. The efficacy is evaluated in terms of changes in HBsAg levels, HBV DNA levels, changes in HBeAg levels (in HBeAg positive subjects only), and HBsAg (in all subjects) or HBeAg (in HBeAg-positive subjects only) seroclearance and/or seroconversion. This study also evaluates the frequency of subjects with biochemical response and HBV virological breakthrough. This study also evaluates the potential effect of Compound A on the pharmacokinetics of nucleos(t)ide analog (NA) when coadministered. This study also evaluates the pharmacokinetics of Compound A when administered as a monotherapy. This study also evaluates the potential effect of NA on the pharmacokinetics of Compound A when coadministered. This study assesses changes in the HBV genome sequence following treatment with Compound A either alone or in combination with a NA.

Finally, this study evaluates the synergistic effects of Compound A and NAs. Synergy, additivity, and antagonism are evaluated using the Pritchard and Shipman model. Synergy or antagonism for a concentration combination is determined based on the following 2 rules: First, the 95% Cl of the mean difference between observed and predicted fraction of inhibition at each concentration combination is calculated. If the lower bound of 95% Cl is larger than zero, then the drug combination would be considered having a synergistic effect; if the upper bound of 95% Cl is less than zero, then the drug combination would be considered having an antagonistic effect; otherwise, no significant antagonism or synergy at this concentration combination. Second, the synergistic or antagonistic effect must have its relative mean difference, the absolute mean difference divided by its corresponding observed mean inhibition, greater than 1%. By doing this, small differences of statistical significance caused by very small variance could be excluded.

The disclosures of each and every patent, patent application, and publication cited herein are hereby incorporated herein by reference in their entirety.

While the invention has been disclosed with reference to specific embodiments, it is apparent that other embodiments and variations of this invention can be devised by others skilled in the art without departing from the true spirit and scope of the invention. The appended claims are intended to be construed to include all such embodiments and equivalent variations.

The invention claimed is:

1. A pharmaceutical composition comprising:
   (a) Compound A:

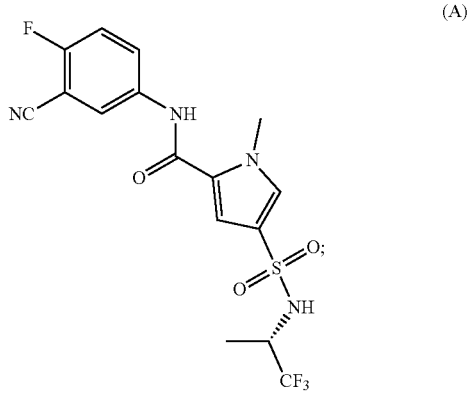 [SMILES: C[C@H](NS(=O)(=O)c1cc(C(=O)Nc2ccc(F)c(C#N)c2)n(C)c1)C(F)(F)F]

or a pharmaceutically acceptable salt thereof, wherein the amount of the compound (A) is 50-500 mg;
   (b) microcrystalline cellulose; and
   (c) silicified microcrystalline cellulose.

2. The pharmaceutical composition of claim 1, wherein the pharmaceutical composition further comprises:
   (d) croscarmellose sodium.

3. The pharmaceutical composition of claim 2, wherein the pharmaceutical composition further comprises:
   (e) colloidal anhydrous silica; and
   (f) magnesium stearate.

4. The pharmaceutical composition of claim 2, wherein the pharmaceutical composition further comprises:
   (g) pre-gelatinized maize starch.

5. The pharmaceutical composition of claim 1, wherein compound (A) is in the form of a spray dried powder.

6. The pharmaceutical composition of claim 5, wherein the pharmaceutical composition further comprises a stabilizer.

7. The pharmaceutical composition of claim 6, wherein the stabilizer is selected from at least one polymer chosen from among HPMC and HPMC-AS.

8. The pharmaceutical composition of claim 7, wherein said at least one polymer is in an amount of 50-1500 mg.

9. The pharmaceutical composition of claim 7, wherein the composition comprises the compound (A) and stabilizer at a ratio of 1:1 by weight.

10. The pharmaceutical composition of claim 7, wherein the composition comprises the compound (A) and stabilizer at a ratio of 1:2 by weight.

11. The pharmaceutical composition of claim 7, wherein the composition comprises the compound (A) and stabilizer at a ratio of 1:3 by weight.

12. The pharmaceutical composition of claim 7, wherein the stabilizer is HMPC.

13. The pharmaceutical composition of claim 7, wherein the stabilizer is HMPC-AS.

14. The pharmaceutical composition of claim 7, wherein the stabilizer is HPMC E5.

15. The pharmaceutical composition of claim 7, wherein the composition comprises 250 mg of Compound (A).

16. The pharmaceutical composition of claim 7, wherein the composition is formulated as a solid formulation, selected from a tablet, a pill or a capsule.

17. The pharmaceutical composition of claim 16, wherein the composition comprises 50 mg of Compound (A).

18. The pharmaceutical composition of claim 16, wherein the composition comprises 100 mg of Compound (A).

* * * * *